United States Patent
Adachi et al.

(10) Patent No.: US 7,282,262 B2
(45) Date of Patent: Oct. 16, 2007

(54) PARTICULATE WATER ABSORBENT CONTAINING WATER ABSORBENT RESIN AS A MAIN COMPONENT

(75) Inventors: Yoshifumi Adachi, Himeji (JP); Takahiro Kitano, Himeji (JP); Hirotama Fujimaru, Kishiwada (JP); Kozo Nogi, Kakogawa (JP)

(73) Assignee: Nippon Shokubai Co., Ltd., Osaka (JP)

( * ) Notice: Subject to any disclaimer, the term of this patent is extended or adjusted under 35 U.S.C. 154(b) by 89 days.

(21) Appl. No.: 10/510,733

(22) PCT Filed: Feb. 9, 2004

(86) PCT No.: PCT/JP2004/001355

§ 371 (c)(1),
(2), (4) Date: Oct. 12, 2004

(87) PCT Pub. No.: WO2004/069936

PCT Pub. Date: Aug. 19, 2004

(65) Prior Publication Data

US 2005/0118423 A1    Jun. 2, 2005

(30) Foreign Application Priority Data

Feb. 10, 2003  (JP) .............................. 2003-032750

(51) Int. Cl.
    *B32B 5/16* (2006.01)
(52) U.S. Cl. .................. 428/402; 428/327; 521/91; 521/92; 521/125

(58) Field of Classification Search ................. 521/91, 521/92, 125; 428/327, 402
See application file for complete search history.

(56) References Cited

U.S. PATENT DOCUMENTS

| | | | |
|---|---|---|---|
| 4,093,776 | A | 6/1978 | Aoki et al. |
| 4,286,082 | A | 8/1981 | Tsubakimoto et al. |
| 4,367,323 | A | 1/1983 | Kitamura et al. |
| 4,446,261 | A | 5/1984 | Yamasaki et al. |
| 4,625,001 | A | 11/1986 | Tsubakimoto et al. |
| 4,683,274 | A | 7/1987 | Nakamura et al. |
| 4,734,478 | A | 3/1988 | Tsubakimoto et al. |
| 4,873,299 | A | 10/1989 | Nowakowsky et al. |
| 4,973,632 | A | 11/1990 | Nagasuna et al. |

(Continued)

FOREIGN PATENT DOCUMENTS

CA    1304533 C    6/1992

(Continued)

OTHER PUBLICATIONS

Russian Patent Office's "Decision to Grant" mailed Sep. 28, 2006 for the Russian Patent Application No. 2004137267.

*Primary Examiner*—H. Thi Le
(74) *Attorney, Agent, or Firm*—Nixon & Vanderhye PC

(57) ABSTRACT

The particulate water absorbent has a cross-linking structure therein, and contains (i) a particulate water absorbent resin having a cross-linking structure on a surface therof and (ii) not less than 0.001 mass % and less than 10 mass % of anorganic acid multivalent metal salt whose molecule contains not less than seven carbon atoms. Futher, the particulate water absorbent contains 90 mass % of particles, whose particle diameter is not less than 106 μm and 850 μm, with respect to the particulate water absorbent.

20 Claims, 5 Drawing Sheets

U.S. PATENT DOCUMENTS

| | | |
|---|---|---|
| 4,985,514 A | 1/1991 | Kimura et al. |
| 4,985,518 A | 1/1991 | Alexander et al. |
| 5,061,259 A | 10/1991 | Goldman et al. |
| 5,124,416 A | 6/1992 | Haruna et al. |
| 5,145,906 A | 9/1992 | Chambers et al. |
| 5,244,735 A | 9/1993 | Kimura et al. |
| 5,250,640 A | 10/1993 | Irie et al. |
| 5,264,495 A | 11/1993 | Irie et al. |
| 5,380,808 A | 1/1995 | Sumiya et al. |
| 5,385,983 A | 1/1995 | Graham |
| 5,409,771 A | 4/1995 | Dahmen et al. |
| 5,453,323 A | 9/1995 | Chambers et al. |
| 5,597,873 A | 1/1997 | Chambers et al. |
| 5,728,742 A | 3/1998 | Staples et al. |
| 5,843,059 A | 12/1998 | Niemeyer et al. |
| 5,981,070 A | 11/1999 | Ishizaki et al. |
| 5,994,440 A | 11/1999 | Staples et al. |
| 6,071,976 A | 6/2000 | Dairoku et al. |
| 6,090,875 A | 7/2000 | Staples et al. |
| RE37,021 E | 1/2001 | Aida |
| 6,228,930 B1 | 5/2001 | Dairoku et al. |
| 6,254,990 B1 | 7/2001 | Ishizaki et al. |
| 6,291,636 B1 | 9/2001 | Miyake et al. |
| 6,399,668 B1 * | 6/2002 | Miyake et al. ............... 521/92 |
| 6,562,879 B1 * | 5/2003 | Hatsuda et al. ............... 521/56 |
| 6,576,713 B2 * | 6/2003 | Ishizaki et al. .......... 525/329.7 |
| 6,720,073 B2 | 4/2004 | Lange et al. |
| 2004/0023589 A1 | 2/2004 | Kainth et al. |
| 2004/0030312 A1 | 2/2004 | Kainth et al. |
| 2004/0044321 A1 | 3/2004 | Kainth et al. |

FOREIGN PATENT DOCUMENTS

| | | |
|---|---|---|
| EP | 0001706 | 5/1979 |
| EP | 0009977 | 4/1980 |
| EP | 0303440 A2 | 5/1989 |
| EP | 0349240 | 1/1990 |
| EP | 0605150 | 7/1994 |
| EP | 0811636 | 12/1997 |
| EP | 0922717 | 6/1999 |
| EP | 0955086 | 11/1999 |
| EP | 0691995 | 4/2000 |
| JP | 59-804459 | 5/1984 |
| JP | 61-58658 | 3/1986 |
| JP | 63-105064 | 5/1988 |
| JP | 63-105064 A | 5/1988 |
| JP | 64-033149 A | 2/1989 |
| JP | 07-224204 | 8/1995 |
| JP | 07-228788 | 8/1995 |
| JP | 07-242709 | 9/1995 |
| JP | 3169133 | 3/2001 |
| JP | 2003-165883 | 6/2003 |
| JP | 2003-165883 A | 6/2003 |
| RU | 2128191 C1 | 3/1999 |

\* cited by examiner

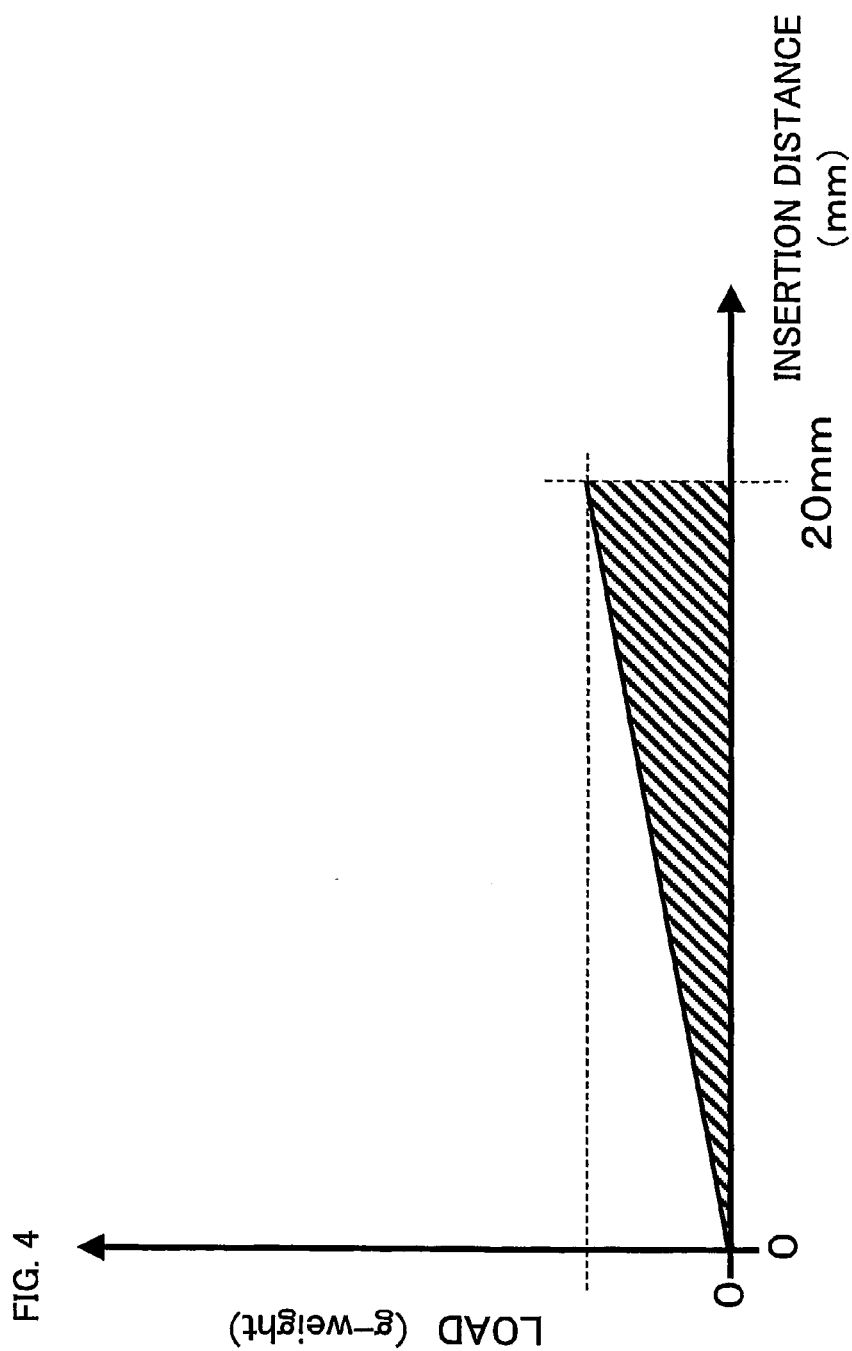

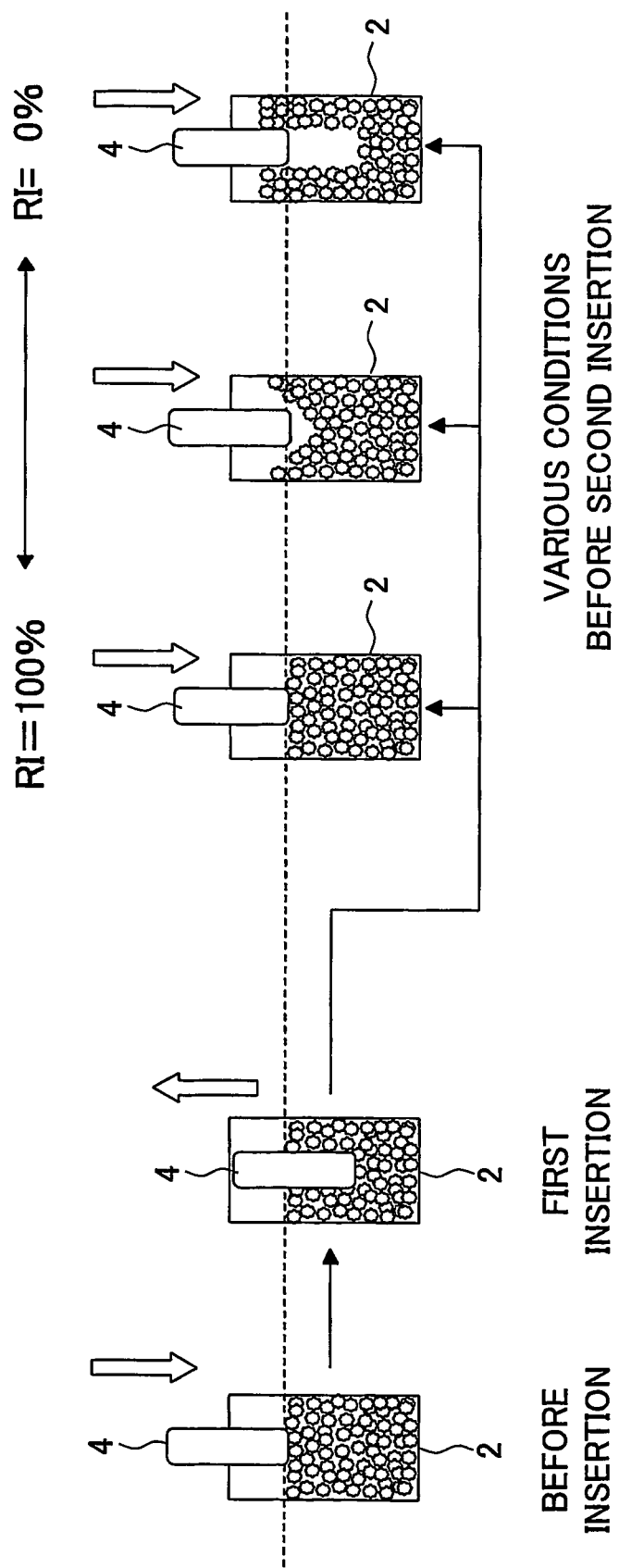

PARTICULATE WATER ABSORBENT CONTAINING WATER ABSORBENT RESIN AS A MAIN COMPONENT

This application is the US national phase of International Application PCT/JP2004/001355 filed 9 Dec. 2004 which designated the U.S. and claims benefit of JP 32750/2003 dated 10 Feb. 2003, the entire content of which is hereby incorporated by reference.

TECHNICAL FIELD

The present invention relates to (i) a particulate water absorbent containing a water absorbent resin as a main component, (ii) an absorbent article using the same, and (iii) a production method of the particulate water absorbent. More specifically, the present invention relates to (i) a particulate water absorbent, (ii) an absorbent article using the same, that are preferably used to absorb a body fluid such as urine and blood and deliver an excellent absorptive capacity, and (iii) a production method of the particulate water absorbent.

BACKGROUND ART

Recently, a water absorbent resin is widely used as a main construction material of sanitary materials (absorbent articles) such as paper diapers, sanitary napkins, incontinence pads and the like, in order to absorb body fluids (e.g. urine, blood, and the like).

Well-known examples of the water absorbent resin are (i) cross-linked partially neutralized polyacrylic acid; (ii) a hydrolyzed starch-acrylonitrile graft polymer; (iii) a neutralized starch-acrylic graft polymer; (iv) a saponified vinyl acetate-acrylic ester copolymer; (v) cross-linked carboxymethylcellulose; (vi) hydrolyzed acrylonitrile copolymer or hydrolyzed acrylamide copolymer, or cross-linked acrylonitrile copolymer or cross-linked acrylamide copolymer; (vii) a cross-linked cationic monomer, (viii) a cross-linked isobutylene-maleic acid copolymer; (ix) a cross-linked body of 2-acrylamide-2-methylpropanesulfonic acid and acrylic acid; (x) and the like. In this manner, the water absorbent resin is a hydrophilic resin which is insolubilized due to its evenly cross-linked structure inside a polymer.

Incidentally, there has conventionally been needs for a water absorbent resin having the following water absorbent properties: (i) a high absorbency for a aqueous liquid such as a body fluid, (ii) an excellent absorption rate, (iii) excellent liquid permeability, and (iv) excellent gel strength of a swollen gel, and (v) an excellent absorptive capacity when water is absorbed from a base material containing a aqueous liquid, (vi) and the like.

Thus, in order to attain the foregoing absorbing properties, usually, surfaces of particles of the water absorbent resin are further cross-linked by using a cross-linking agent or the like, thereby causing the particles to have a cross-linking density gradient. Thus, (i) a water-absorption rate of the water absorbent resin is improved, (ii) generation of fish eye is prevented, (iii) gel strength is improved, (iv) an absorbency of the water absorbent resin under pressure is improved, (v) gel blocking is prevented, and (vi) liquid permeability is improved.

For example, surface cross-linking processes for causing a vicinity of particle surfaces of the water absorbent resin to have a cross-linking density gradient are described in Patent Document 1 (European Patent No. 0349240), Patent Document 2 (European Patent No. 0605150), Patent Document 3 (Japanese Publication for Unexamined Patent Application, Tokukaihei 7-242709), Patent Document 4 (Japanese Publication for Unexamined Patent Application, Tokukaihei 7-224304), Patent Document 5 (U.S. Pat. No. 5,409,771), Patent Document 6 (U.S. Pat. No. 5,597,873), Patent Document 7 (U.S. Pat. No. 5,385,983), and the like. In addition to the foregoing methods recited in the patent Documents, a water absorbent including a water absorbent resin and metal soap in order to improve liquid permeability, is described in Patent Document 8 (Japanese Publication for Unexamined Patent Application, Tokukaisho 61-58658).

Moreover, there are needs for such a water absorbent resin which not only has the foregoing water absorbent properties, but also has the following advantages: (i) The water absorbent resin has excellent fluidity at the time of production and transportation of the water absorbent resin, at the time of production of an absorber by processing the water absorbent resin and a fiber base material or the like, and at the time of moisture absorption, so that the water absorbent resin rarely adheres to an apparatus or the like; and (ii) The water absorbent resin is not significantly deteriorated in terms of water absorbent properties, when subjected to a mechanical shock. As an attempt to produce water absorbent resin having excellent fluidity at the time of moisture absorption, a water absorbent in which an inorganic substance such as amorphous silicon dioxide, kaoline, or the like is added, is proposed. Specifically, for example, art related to a water absorbent including powder of an inorganic substance and powder of a water absorbent resin is disclosed in Patent Document 9 (U.S. Pat. No. 4,734,478), Patent Document 10 (Japanese Publication for Unexamined Patent Application, Tokukaisho 59-80458), and Patent Document 11 (U.S. Pat. No. 5,453,323).

Further, for example, a water absorbent in which stearic acid and powder of an inorganic substance are added as additives is described in Patent Document 12 (Japanese Publication for Unexamined Patent Application, Tokukaisho 63-105064), and a water absorbent in which quaternary ammonium salt is added as additives is described in Patent Document 13 (U.S. Pat. No. 5,728,742). Moreover, a water absorbent in which oxalic acid (salt) and a multivalent metal compound such as (i) metal oxide such as silicon oxide or the like, (ii) metal sulfate such as calcium sulfate or the like, or (iii) the like are added, is described in Patent Document 14 (Japanese Publication for Unexamined Patent Application, Tokukaihei 7-228788).

Moreover, a water absorbent resin compound in which polyethyleneglycol, polypropyleneglycol, or the like are added is disclosed in Patent Document 16 (European Patent No. 0001706).

However, the water absorbents recited in the foregoing Patent Documents have the following various problems. That is, as to the water absorbent resins recited in the Patent Documents 1 to 8, the fluidity at the time of moisture absorption is insufficient. Further, as to the water absorbents recited in the Patent Documents 9 to 11, an inorganic powder is used in order to improve the fluidity at the time of moisture absorption, so that the water absorbent properties are deteriorated due to the hardness of the inorganic substance when the water absorbent resin is subjected to a mechanical shock (damage). Therefore, absorbent articles using the water absorbents recited in the Patent Documents 9 to 11 cannot attain sufficient absorbing properties.

Further, as to the water absorbents recited in the Patent Documents 12 and 13, there is a problem of safety because there is a possibility that, when the water absorbent is used as an absorbent article, the additive contained in the water absorbent liquates out into an aqueous liquid such as urine and the like absorbed by the water absorbent. Therefore, in the case of using the water absorbents recited in the Patent Documents 12 and 13 as a material for a paper diaper or the like for example, a aqueous liquid such as urine is hard to diffuse in the whole water absorbent. As a result, a return amount of the aqueous liquid absorbed by the water-absorbent provided in the paper diaper is increased, so that the water absorbent properties are deteriorated.

Further, as to the water absorbent recited in the Patent Document 14, the oxalic acid (salt) is contained as the additive, so that there is a problem of safety concerning the oxalic acid. Moreover, when the water absorbent resin is subjected to a mechanical shock, it is difficult to alleviate (absorb) the mechanical shock, and the water absorbent resin is even damaged, so that the water absorbent properties are significantly deteriorated. This is because the oxalic acid (salt) and an inorganic substance such as a multivalent metal compound contained as the additive are hard.

Further, in the case of using the inorganic substance as described above, the fluidity at the time of moisture absorption is improved, but there is the following problem: powder fluidity of the water absorbent is deteriorated under such a dry condition that a moisture content is less than 10 mass %.

On the other hand, when the water absorbents recited in the Patent Documents 15 and 16 are used, it is possible to slightly reduce frictional resistance of the water absorbent. However, also in the water absorbents recited in the Patent Documents 15 and 16, the powder fluidity (anti-caking) at the time of moisture fluidity and the powder fluidity under such a dry condition that the moisture content is less than 20 mass %, particularly less than 10 mass %, are insufficient. At the time of moisture absorption, viscosity occurs among particles, so that this results in blocking or caking. As a result, the powder fluidity is deteriorated. Further, the particles themselves have a high frictional coefficient also in a dry state. Therefore, in the water absorbent under the dry condition, the frictional resistance is increased, so that it is difficult to smoothly transport and carry the water absorbent at the time of production or the like of the water absorbent.

DISCLOSURE OF INVENTION

The object of the present invention is to obtain a particulate water absorbent which has the following properties: (1) The particulate water absorbent agent has excellent fluidity at the time of moisture absorption and even under such a dry condition that a moisture content is 0 to 20 mass %, and it is easy to handle the particulate water absorbent agent at the time of production and transportation thereof; (2) The particulate water absorbent agent is not significantly deteriorated in terms of water absorbent properties and the fluidity at the time of moisture absorption, when subjected to a mechanical shock at the time of production and transportation thereof; and (3) The particulate water absorbent agent has stable and superior water absorbent properties.

As a result of earnest study in terms of the foregoing problems, the present inventors found that: it is possible to realize excellent fluidity at the time of moisture absorption when the particulate water absorbent is provided in an absorbent article such as a diaper, and it is possible to keep the water absorbent properties even when receiving a mechanical shock, and it is possible to obtain the excellent water absorbent properties, by using a particulate water absorbent containing (1) a specific amount of water absorbent resin particles, having a specific particle size distribution, whose surface is cross-linked and (2) a specific amount of an organic acid multivalent metal salt whose molecule contains seven or more carbon atoms. Further, the present inventors found that: in addition to the excellent water absorbent properties, it is possible to prevent damage, brought about in processes of producing the particulate water absorbent as an absorbent article, from deteriorating the water absorbent properties, by using a particulate water absorbent having specific parameters.

That is, the particulate water absorbent of the present invention is a particulate water absorbent which includes, as a main component, a water absorbent resin in which a polymer obtained by polymerizing an unsaturated monomer has a cross-linking structure therein, wherein: the water absorbent resin is a particulate water absorbent resin which has a cross-linking structure on a surface thereof, and the particulate water absorbent contains not less than 90 mass % and not more than 100 mass % of particles, whose particle diameter is not less than 106 μm and less than 850 μm, with respect to the particulate water absorbent, and the particulate water absorbent resin further contains not less than 0.001 mass % and less than 10 mass % of organic acid multivalent metal salt, whose molecule contains not less than seven carbon atoms, with respect to the water absorbent resin.

Further, the particulate water absorbent of the present invention may be a particulate water absorbent which includes, as a main component, a water absorbent resin in which a polymer obtained by polymerizing an unsaturated monomer has a cross-linking structure therein, wherein: the water absorbent resin is a particulate water absorbent resin which has a cross-linking structure on a surface thereof, and the particulate water absorbent resin further contains not less than 0.001 mass % and less than 10 mass % of organic acid multivalent metal salt, whose molecule contains not less than seven carbon atoms, with respect to the water absorbent resin, and a moisture absorption fluidity index ranges from not less than 90 mass % to not more than 100 mass %.

Further, the particulate water absorbent of the present invention may be a particulate water absorbent which includes, as a main component, a water absorbent resin in which a polymer obtained by polymerizing an unsaturated monomer has a cross-linking structure therein, wherein: the water absorbent resin is a particulate water absorbent resin which has a cross-linking structure on a surface thereof, and a moisture absorption fluidity index X ranges from not less than 90 mass % to not more than 100 mass %, and a moisture absorption fluidity retention index defined by (Equation 1) below is not less than 0.95, the moisture absorption fluidity retention index=Y/X ... (Equation 1), where X is the moisture absorption fluidity index X and Y is a moisture absorption fluidity index Y after applying a predetermined shock to the particulate water absorbent.

Further, the particulate water absorbent of the present invention may be a particulate water absorbent which includes, as a main component, a water absorbent resin in which a polymer obtained by polymerizing an unsaturated monomer has a cross-linking structure therein, wherein: the water absorbent resin is a water absorbent resin constituted of particles each of which has a shape other than a shape of a spherical primary particle and a shape of an ellipsoidal primary particle, and when the particulate water absorbent is immersed in 0.9 mass % of a sodium chloride aqueous liquid under a pressure of 2.06 kPa, an absorbency under pressure is not less than 20 g/g, and a maximum insertion load which is a maximum load required in inserting an insertion member to a predetermined distance of the particulate water absorbent is not less than 0 g-weight and not more than 1,000 g-weight, and an insertion work which is a work in inserting the insertion member to the predetermined distance of the particulate water absorbent is not less than 0 g-weight×mm and not more than 10,000 g-weight×mm.

Further, the particulate water absorbent of the present invention may be a water absorbent which includes, as a main component, a water absorbent resin in which a polymer obtained by polymerizing an unsaturated monomer has a cross-linking structure therein, wherein: the water absorbent resin is a water absorbent resin constituted of particles each of which has a shape other than a shape of a spherical primary particle and a shape of an ellipsoidal primary particle, and when the particulate water absorbent is immersed in 0.9 mass % of a sodium chloride aqueous liquid under a pressure of 2.06 kPa, an absorbency under pressure is not less than 20 g/g, and an insertion work which is a work in inserting the insertion member to the predetermined distance of the particulate water absorbent is not less than 0 g-weight×mm and not more than 5,000 g-weight×mm, and a recovery index represented by a ratio of (i) a reinsertion work, which is a work in pulling out and reinserting the insertion member after inserting the insertion member to the predetermined distance of the particulate water absorbent, with respect to (ii) the insertion work is not less than 55%.

According to the foregoing arrangement, it is possible to provide a particulate water absorbent, which can prevent blocking and caking at the time of moisture absorption, and has preferable powder fluidity, and is easy to handle. Further, according to the present invention, it is possible to prevent process damage brought about in (i) apparatuses for producing a particulate water absorbent and an absorbent article or the like using the particulate water absorbent, (ii) production steps, and (iii) pipes or the like used at the time of production and transportation of the particulate water absorbent. Thus, it is possible to provide a superior absorbent article, and it is easier to design an amount of the particulate water absorbent used in the absorbent article in order to obtain a desired absorption amount.

The following description will sufficiently clarify further objects, characteristics, and excellent points of the present invention. Further, advantages of the invention will be clarified with reference to the ensuing detailed description taken in conjunction with the accompanying drawings.

BRIEF DESCRIPTION OF DRAWINGS

FIG. 4 is a graph showing an example of how a load required in inserting the insertion probe into a particle layer varies for each insertion distance of the insertion probe.

FIG. 5 is a schematic diagram showing how a recovery index is measured.

BEST MODE FOR CARRYING OUT THE INVENTION

Figure 1:
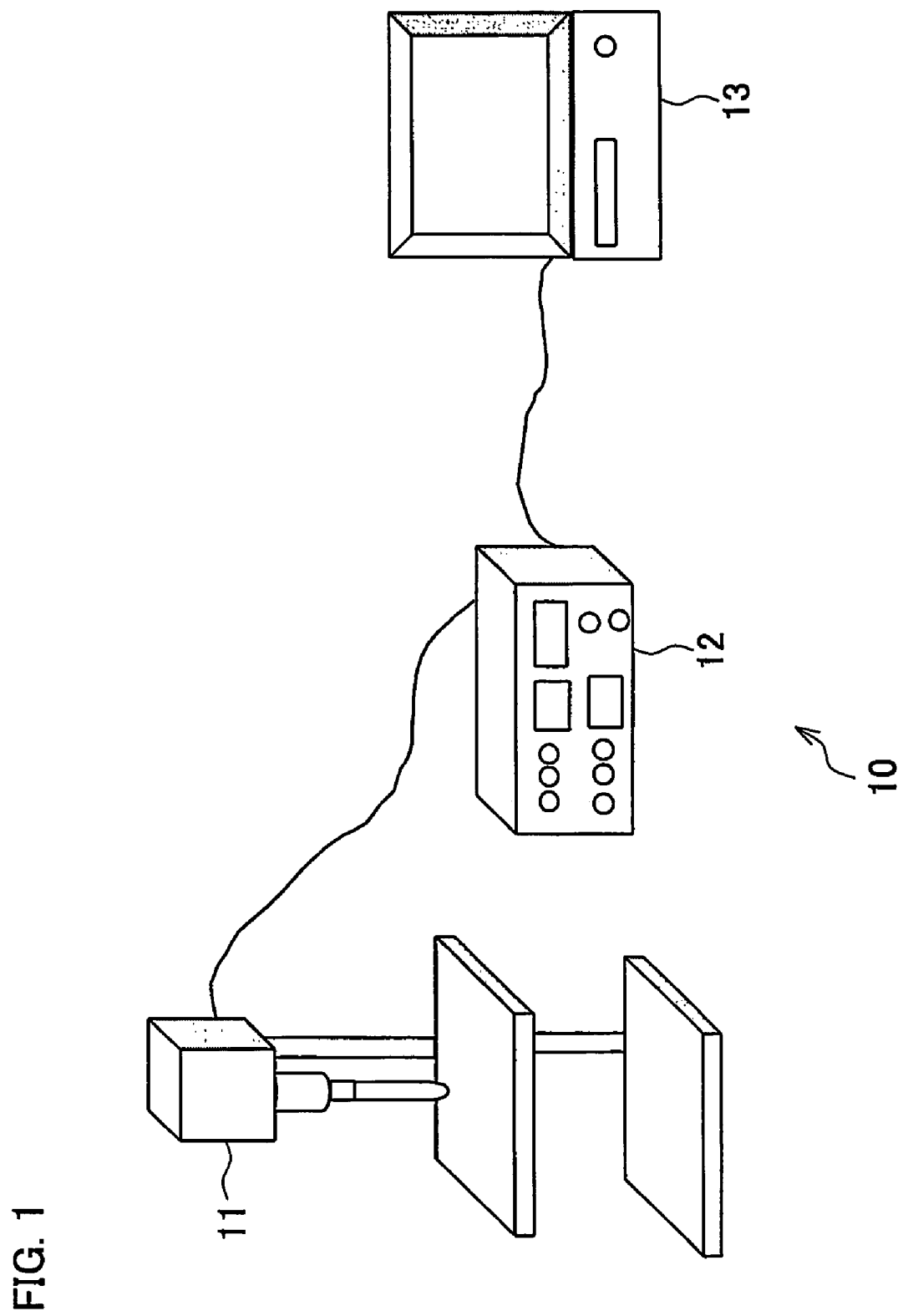
FIG. 1 is a perspective view schematically showing an arrangement of a measuring device for measuring a maximum insertion load, an insertion work, and an insertion distance.

Detailed description is made below as to a particulate water absorbent and an absorbent article using the same according to the present invention. While the invention is susceptible to various modifications and alternative forms, specific embodiments thereof will be described below by way of example. It should be understood, however, that it is not intended to limit the invention to the particular forms disclosed, but on the contrary, the invention is to cover all modifications, equivalents, and alternatives falling within the scope of the invention as defined in the appended claims.

The particulate water absorbent of the present invention is used to absorb water, various aqueous solution, aqueous liquid such as urine and blood, and contains generally 80 mass % or more, more preferably 90 mass % or more of a pure resin component of a water absorbent resin, with respect to a solid component of the water absorbent resin, as a main component out of all the components contained in the particulate water absorbent. The particulate water absorbent includes a water absorbent resin and multivalent metal salt of organic acid (hereinafter, referred to organic acid multivalent metal salt), and may further include a compound (hereinafter, referred to as other component) other than the water absorbent resin and the organic acid multivalent metal salt.

The organic acid multivalent metal salt is added to the particulate water absorbent, and the particulate water absorbent is made to have specific parameters, so that the particulate water absorbent shows excellent fluidity as powder and excellent absorbent properties, when receiving a mechanical shock, under a dry condition and at the time of moisture absorption.

The following description will detail (i) a water absorbent resin contained in the particulate water absorbent of the present invention, (ii) organic acid multivalent metal salt, (iii) the particulate water absorbent, (iv) a parameter at which it is possible to exhibit the excellent absorbent properties and fluidity as powder, and (v) an absorbent article using the particulate water absorbent. Note that, in the present specification, "mass" and "weight" are synonymously used.

[Water Absorbent Resin]

The water absorbent resin of the present invention is a cross-linked polymer that has water-swelling property and water insolubility and thus can form a hydrogel. Here, the water-swelling property is such a property that: by immersing the water absorbent rein into ion-exchange water, a substance having the property absorbs an amount of aqueous liquid greater than its own weight by a factor of at least 5 or more, preferably by a factor of 50 to 1000. Further, the water insolubility is such a property that: in a water absorbent resin having the property, usually 0 to 50 mass %, preferably 0 to 30 mass %, more preferably 0 to 25 mass %, especially preferably 0 to 15 mass %, and most preferably 0 to 10 mass % of a substantially non-cross-linked water soluble component (water soluble macro molecules) is contained. How to measure the water-swelling property and water insolubility are specifically defined in Examples described later.

Further, the cross-linking polymer is a polymer having a cross-linking structure (hereinafter, referred to as internally cross-linking structure) in polymer obtained by polymerizing an unsaturated monomer for the sake of better absorbent properties. Moreover, the water absorbent resin may be subjected to such a surface cross-linking treatment that: surfaces of particles of the water absorbent resin are cross-linked, or may be free from the surface cross-linking treatment. In order to obtain the excellent absorbent properties, it is preferable to perform the surface cross-linking process. Note that, hereinafter, a water absorbent resin which has not been subjected to the surface cross-linking treatment is sometimes referred to as a water absorbent resin precursor.

Examples of the water absorbent resin constituted of the cross-linking polymer include: a partly neutralized polyacrylic polymer, a hydrolyzed starch-acrylonitril graft polymer, a starch-acrylic acid graft polymer, a saponificated acetic vinyl-acryl ester copolymer, hydrolyzed acrylonitrile copolymer or hydrolyzed acrylamide copolymer, or cross-linked acrylonitrile copolymer or cross-linked acrylamide copolymer, a cross-linked denatured polyvinyl alcohol having a carboxyl group, a cross-linked isobutylene-maleic anhydride copolymer, and the like. The resin listed above may be used solely or two or more kinds of the resin may be used in combination. It is preferable to use the partly neutralized polyacrylic polymer.

The water absorbent resin constituted of the cross-linking polymer is obtained by polymerizing and cross-linking an unsaturated monomer, and is subjected to the surface cross-linking treatment as required. The following description will explain an unsaturated monomer, a cross-linking monomer, a polymerization initiator, and a production method of the unsaturated monomer (polymerization method, drying treatment, surface cross-linking treatment) that are used to produce the water absorbent resin.

<Unsaturated Monomer>

As the unsaturated monomer used to obtain the water absorbent resin contained in the particulate water absorbent of the present invention, it is preferable to use a monomer by which it is possible to obtain a desired cross-linking polymer.

For example, in case where the cross-linking polymer is a partly neutralized polyacrylic polymer, it is preferable to use acrylic acid and/or its salt (neutralized acrylic acid) as main components. And, (i) acrylic acid and/or its salt, and (ii) another monomer may be used in combination as copolymer components. Thus, it is possible to give not only the water absorbent properties but also special properties such as an antibacterial property and a deodorant property to the water absorbent resin obtained as a final product, and it is possible to obtain the water absorbent resin at lower cost.

As a copolymer component, examples of the aforementioned another unsaturated monomer include water-soluble or hydrophobic unsaturated monomers, and the like, such as methacrylic acid, maleic acid (or maleic anhydride), fumaric acid, crotonic acid, itaconic acid, vinyl sulfonic acid, 2-(meth)acrylamide-2-methylpropanesulfonate, (meth)acryloxyalkane sulfonic acids and its alkaline metal salts, its ammonium salts, N-vinyl-2-pyridone, N-viniyl acetamide, (meth)acrylamide, N-isopropyl (meth)acrylamide, N,N-dimethyl (meth)acrylamide, 2-hydroxyethyl(meth)acrylate, methoxypolyethylene glycol(meth)acrylate, polyethylene glycol (meth)acrylate, isobutylene, lauryl(meth)acrylate, and the like.

Note that, in case where the monomer is an unsaturated monomer having an acid group as the unsaturated monomer and another unsaturated monomer that is used in combination with the acrylic acid and/or its salt, its salt may be an alkaline metal salt, an alkaline earth metal salt, or an ammonium salt. Meanwhile a sodium salt or a potassium salt is preferable above all because (i) the sodium salt and potassium salt are easily obtained industrially, (ii) the sodium salt and potassium salt are harmless, and (iii) use of the sodium salt and/or potassium salt gives better property to the water absorbent resin obtained and effects the other advantages.

In case where the aforementioned another unsaturated monomer is additionally used, the monomer other than acrylic acid (salt) is preferably 0 to 30 mol %, more preferably 0 to 10 mol %, and most preferably 0 to 5 mol %, with respect to a total number of moles of all the unsaturated monomers used to obtain the water absorbent resin. In other words, it is preferable that a total number of moles of acrylic acid and its salt that are used as main components is 70 to 100 mol %, preferably 90 to 100 mol %, more preferably 95 to 100 mol % with respect to a total number of moles of all the unsaturated monomers used to obtain the water absorbent resin.

Further, in case where the cross-linking polymer is a partly neutralized polyacrylic polymer, it is preferable that a constitutional unit of the partly neutralized polyacrylic polymer is as follows: the unsaturated monomer contains acrylic acid in a range of 0 mol % to 50 mol % and acrylate in a range of 100 mol % to 50 mol % (the sum of acrylic acid and acrylate is 100 mol % or less). It is more preferable that the constitutional unit of the partly neutralized polyacrylic polymer is as follows: the unsaturated monomer contains acrylic acid in a range of 10 mol % to 40 mol % and acrylate in a range of 90 mol % to 60 mol %. In other words, it is preferable that a neutralization ratio which is a molar ratio of acrylate with respect to a total amount of acrylic acid and acrylate ranges from 50 to 100 mol %, and it is more preferable that the neutralization ratio ranges from 60 to 90 mol %.

The salt of acrylic acid may be prepared by neutralizing monomeric acrylic acid before polymerizing the monomer, or by neutralizing acrylic acid in and after polymerization. The salt may be prepared by using those methods in combination. Further, the salt of acrylic acid may be prepared by mixing acrylic acid and acrylate.

<Cross-linking Monomer (Internal Cross-linking Agent)>

The water absorbent resin of the present invention is a cross-linking polymer having an internally cross-linking structure. When the water absorbent resin has water-insolubility and a water-swelling property, it is regarded as having an internally cross-linking structure. Thus, the internally cross-linking structure of the water absorbent resin may be obtained by causing an unsaturated monomer to be self-cross-linked without using a cross-linking monomer. However, it is more preferable that the water absorbent resin is obtained by copolymerizing or reacting the unsaturated monomer with the cross-linking monomer. Here, the cross-linking monomer which functions as an internal cross-linking agent has two or more polymerizable unsaturated groups contained in one molecule thereof or has two or more reactive groups.

Examples of such an internal cross-linking agent includes N,N'-methylenebis(meth)acrylamide, (poly)ethyleneglycol di(meth)acrylate, (poly)propyleneglycol di(meth)acrylate, trimethylolpropanetri(meth)acrylate, glyceroltri(meth)acrylate, glycerolacrylatemethacrylate, ethyleneoxide denatured trimethylolpropanetri(meth)acrylate, pentaerythritolhexa (meth)acrylate, triallyl cyanurate, triallyl isocyanurate, triallyl phosphate, triallyl amine, poly(meth)allyloxyalkane, (poly)ethyleneglycoldiglycidylether, glyceroldiglycidylether, ethylene glycol, polyethylene glycol, propylene glycol, glycerine, pentaerythritol, ethylenediamine, ethylene carbonate, propylene carbonate, polyethyleneimine, and glycidyl(meth)acrylate, and the like.

These internal cross-linking agents may be used either individually or in a suitable combination of two or more kinds. The internal cross-linking agent may be added to the reaction system either at once or in separate doses. When using one or more internal cross-linking agents, it is preferable that a cross-linking monomer including not less than two polymerizable unsaturated groups is always used for the polymerization, taking into account the absorption characteristics or other properties of the product water absorbent.

For desirable properties of the water absorbent resin, the amount of internal cross-linking agent used is preferably 0.001 to 2 mol %, more preferably 0.005 to 0.5 mol %, further preferably 0.01 to 0.2 mol %, and particularly preferably 0.03 to 0.15 mol %, all with respect to a total number of moles of all the unsaturated monomers used to obtain the water absorbent resin. In case the amount of the internal cross-linking agent to be added is less than 0.001 mol %, or in case the amount is more than 2 mol %, there is a possibility that a sufficient absorbent property cannot be attained, so that this is not preferable.

When the internal cross-linking agent is used to form a cross-linked structure inside the water absorbent resin, the internal cross-linking agent is added to the reaction system before, during, or after the polymerization of the unsaturated monomer, or after the neutralization of the unsaturated monomer or the polymer.

<Polymerization Initiator>

The water absorbent resin of the present invention is obtained by using a polymerization initiator in polymerizing the unsaturated monomer. As the polymerization initiator, for example, a radical polymerization initiator such as potassium persulfate, ammonium persulfate, sodium persulfate, potassium peracetic, sodium peracetic, potassium percarbonate, sodium percarbonate, t-butylhydroperoxide, hydrogen peroxide, and 2,2'-azobis (2-amidino-propane) dihydrochloride, or a photopolymerization initiator such as 2-hydroxy-2-methyl-1-phenyl-propane-1-one may be used.

It is preferable that an amount of the polymerization initiator is usually in a range of 0.001 mol % to 2 mol %, and preferably in a range of 0.01 mol % to 0.1 mol % with respect to the total number of moles of all the unsaturated monomers used to obtain the water absorbent resin. If the polymerization initiator is less than 0.001 mol %, an amount of monomer not reacted and left over (left-over amount) is increased. On the other hand, if the amount of the polymerization initiator is more than 2 mol %, it becomes difficult to control the polymerization. Thus, neither of the amount of the polymerization initiator less than 0.001 mol % nor the amount more than 2 mol % is preferable.

<Production Method of Water Absorbent Resin>

(Polymerization Method)

For the polymerization of the monomer (unsaturated monomer, another unsaturated monomer, cross-linking polymer, and the like) to obtain the water absorbent resin of the present invention, bulk polymerization or precipitation polymerization may be performed. However, in consideration of the performance of the water absorbent resin, controllability of polymerization, and absorption characteristics of a swelling gel, more preferable methods of polymerization are aqueous polymerization and reversed suspension polymerization, using an aqueous solution of the monomer.

When an aqueous solution of the monomer is used, the concentration of the monomer in the aqueous solution (hereinafter, "monomer aqueous solution") is determined in accordance with a temperature of the solution and a type of the monomer and hence is not limited to any particular value. However, the concentration is preferably within 10 to 70 mass %, and more preferably 20 to 60 mass %.

The polymerization of the monomer is initiated by using the aforementioned polymerization initiator. Besides the polymerization initiator, an activating energy ray, such as ultraviolet light, an electron ray, and a γ ray, may be used solely or in combination with the polymerization initiator. Note that, which temperature the polymerization is initiated is selected as required depending on which kind of polymerization initiator is used. However, it is preferable that the polymerization is initiated at a temperature in a range of 15° C. to 130° C., and it is more preferable that the polymerization is initiated at a temperature in a range of 20° C. to 120° C. If the polymerization is initiated at temperature out of the ranges, there is a possibility that the left-over amount of the monomer is increased or self-cross-linkage excessively takes place thereby causing the water absorbent resin to have a low water absorbent property.

The reverse phase suspension polymerization is a polymerization method that is carried out by suspending the monomer aqueous solution in a hydrophobic organic solvent. For example, the reverse phase suspension polymerization is described in documents such as U.S. Pat. No. 4,093,776, No. 4,367,323, No. 4,446,261, No. 4,683,274, and No. 5,244,735, for example.

Further, the aqueous solution polymerization is a polymerization method in which the polymerization is carried out by using the monomer aqueous solution without using a dispersion solvent. For example, the aqueous solution polymerization is described in documents such as U.S. Pat. No. 4,625,001, No. 4,873,299, No. 4,286,082, No. 4,973,632, No. 4,985,518, No. 5,124,416, No. 5,250,640, No. 5,264,495, No. 5,145,906, and No. 5,380,808, and documents such as European Patent No. 0,811,636, No. 0,955,086, and No. 0,922,717. Note that, when performing aqueous polymerization, a solvent other than water may be used as required. The type of solvent used together is not particularly limited.

Thus, by using the monomer and the polymerization initiator that are described as examples in accordance with the polymerization method recited in each document, it is possible to obtain the water absorbent resin of the present invention.

(Drying)

In general, the polymer obtained by polymerizing a monomer in accordance with the foregoing polymerization method is a cross-linked polymer in a form of a water-containing gel (water-containing gel-form cross-linked polymer). If necessary, the water-containing gel-form cross-linked polymer is dried. Note that, particularly in case of performing water soluble polymerization, it is general that the cross-linked polymer is pulverized before or after drying the water-containing gel-form cross-linked polymer.

In case where a hot-air drying is adopted in the drying, the hot-air drying is carried out usually with hot air whose temperature is in a range of 60° C. to 250° C., preferably in a range of 100° C. to 220° C., and more preferably in a range of 120° C. to 200° C. How long the drying is carried out (drying time) depends on how much surface area and moisture content the polymer has and which type of a dryer is used, so that the drying time is so set, as required, that the polymer will have a target moisture content after drying, for example, the drying time is set to be within a range from one minute to 5 hours as required.

The moisture content of the water absorbent resin that can be obtained by the drying is not particularly limited (As the term is used herein, the "moisture content" is defined by the amount of water contained in the water absorbent resin as measured by the proportion of the lost weight after drying in the mass of the water absorbent resin before drying when 1 g of the water absorbent resin is dried for 3 hours at 180° C.).

However, for better property of the particulate water absorbent of the present invention which contains the water absorbent resin as a main component, it is preferable to control the moisture content so that the polymer is in a powder form and flowable even at room temperatures. That is, the water absorbent has a moisture content generally in a range of 0 to 30 mass %, more preferably in a range of 0 to 20 mass %, further preferably in a range of 0 to 15 mass %, still further preferably in a range of 0.3 to 15 mass %, and especially preferably in a range of 0.5 to 10 mass % (As the term is used herein, the "moisture content" is defined by the amount of water contained in the water absorbent resin as measured by the proportion of the lost weight after drying in the mass of the water absorbent resin before drying when 1 g of the water absorbent resin is dried for 3 hours at 180° C.). Thus, it is preferable to obtain the water absorbent resin by drying the water-containing gel-form cross-linked polymer so as to obtain the water absorbent having the moisture content in the foregoing range.

Note that, in case where the polymerization is carried out by the reverse phase suspension polymerization, the water-containing gel-form cross-linked polymer obtained after polymerization reaction may be dried without pulverization as follows. That is, the water-containing gel-form cross-linked polymer is dispersed in an organic solvent of a hydrocarbon such as hexane and the like, and azeotropically dried so that the water-containing gel-form cross-linked polymer has a moisture content of 40 mass % or less, and preferably 30 mass % or less. After that, the water-containing gel-form cross-linked polymer is separated by decantation or volatilization, thereby obtaining the water absorbent resin of the present invention. Note that, the water absorbent resin separated from the organic solvent may be further dried as required.

As long as it is possible to attain the target moisture content, the drying is not particularly limited, and it is possible to adopt various methods. Specifically, the drying methods that can be adopted here are, for example, thermal drying, hot air drying, drying under reduced pressure, infrared drying, microwave drying, drying by azeotropy with a hydrophobic organic solvent, high-moisture drying in which a high temperature steam is used, and the like drying methods.

(Surface Cross-linking Treatment)

As described above, the water absorbent resin of the present invention can be obtained by performing the cross-linking polymerization and the drying and by performing the pulverization as required, and it is preferable to perform a step of cross-linking (secondary cross-linking) a surface of the water absorbent resin so as to enhance the cross-linking density in a vicinity of a surface of the water absorbent resin so that properties of the water absorbent resin is improved. Hereinafter, the water absorbent resin which has not been subjected to the surface cross-linking treatment is referred to as a water absorbent resin precursor so as to distinguish from the water absorbent resin whose surface has been cross-linked. Note that, the water absorbent resin of the present invention is the water absorbent resin precursor and/or the water absorbent resin whose surface has been cross-linked.

There are various kinds of surface cross-linking agents for cross-linking the surface. For attaining better properties of the obtained water absorbent resin, it is preferable to use one kind or two or more kinds of the following cross-linking agents: (a) multivalent alcohol compounds, (b) epoxy compounds, (c) multivalent amine compounds, (d) products of condensation of the multivalent amine compounds with haloepoxy compounds, (e) oxazoline compounds, (f) mono, di, or poly oxazolidine compounds, (g) multivalent metal salts, (h) alkylene carbonate compounds, (i) and the like.

More specifically, it is preferable to use the surface cross-linking agents listed up in U.S. Pat. No. 6,228,930, No. 6,071,976, and No. 6,254,990, for example. That is, the surface cross-linking agent may be (a) multivalent alcohol compounds such as monoethylene glycol, diethylene glycol, triethylene glycol, tetraethylene glycol, polyethylene glycol, monopropylene glycol, 1,3-propanediol, dipropylene glycol, 2,3,4-trimethyl-1,3-pentanediol, polypropylene glycol, glycerin, polyglycerin, 2-butene-1,4-diol, 1,4-butanediol, 1,3-butanediol, 1,5-pentanediol, 1,6-hexanediol, 1,2-cyclohexanedimethanol, and the like; (b) epoxy compounds such as ethylene glycol diglycidyl ether, glycidol, and the like; (c) multivalent amine compounds such as ethylenediamine, diethylenetriamine, triethylenetetramine, tetraethylenepentamine, pentaethylenehexamine, polyethyleneimine, polyamindepolyamine and the like; (d) haloepoxy compounds such as epichlorohydrin, epibromohydrin, α-methylepichlorohydrin, and the like; (e) products of condensation of the multivalent amine compounds with the haloepoxy compounds; (f) oxazolidione compounds such as 2-oxazolidione and the like; (g) alkylenecarbonate compounds such as ethylene carbonate and the like; (h) and the like.

For attaining better properties of the water absorbent resin, it is preferable to use at least one of the multivalent alcohols among the cross-linking agent. It is preferable that the multivalent alcohols to be used have two to ten carbon atoms, and preferably three to eight carbon atoms.

An amount of the surface cross-linking agent depends on which type of the surface cross-linking agent is used, or how the water absorbent resin precursor and the surface cross-linking agent are combined with each other. However, the amount of the surface cross-linking agent is preferably in a range of 0.001 parts to 10 parts by mass, and more preferably in a range of 0.01 parts to 5 parts by mass, with respect to 100 parts by mass of the water absorbent resin precursor.

In performing the surface cross-linking treatment, it is preferable to use water in combination with the surface cross-linking agent. In this case, an amount of the water to be used depends on how much moisture content of the water absorbent precursor to be used has. In general, with respect to 100 parts by mass of the water absorbent resin precursor, the amount of the water to be used is in a range of 0.5 parts to 20 parts by mass, and preferably 0.5 parts to 10 parts by mass.

It is possible to use a hydrophilic organic solvent other than water, and it is possible to use a mixed solvent of water and hydrophilic organic solvent. An amount of the hydrophilic organic solvent or the mixed solvent to be used is in a range of 0 part to 10 pars by mass, preferably in a range of 0 part to 5 parts by mass, and more preferably in a range of 0 part to 3 parts by mass with respect to 100 parts by mass of the water absorbent resin precursor.

Various methods can be adopted in adding the surface cross-linking agent, the following mixing method is preferable: in advance, the surface cross-linking agent is mixed with water and/or the hydrophilic organic solvent as required, and the mixture is dropped to the water absorbent resin precursor. And the following method is more preferable: in advance, the surface cross-linking agent is mixed with water and/or the hydrophilic organic solvent as required, and the mixture is sprayed to the water absorbent resin precursor. An average diameter of liquid droplets to be sprayed is preferably 0.1 to 300 μm, and more preferably 1 to 200 μm.

As to a mixing apparatus for use in mixing the water absorbent resin precursor, the surface cross-linking agent, and water or the hydrophilic organic solvent, it is preferable that the mixing apparatus has a large mixing power in order that these compounds are mixed evenly and thoroughly. Examples of mixing apparatuses that can be preferably used as the mixing apparatus are: a cylindrical mixer, double-wall conical mixer, a high-speed stirring mixer, a V-shaped mixer, a ribbon blender, a screw mixer, a double-arm kneader, a crush-type kneader, a rotary mixer, an air current mixer, a turbulizer, batch-type Lödige mixer, continuous Lödige mixer, and the like apparatuses.

After mixing the surface cross-linking agent with the water absorbent resin precursor, it is preferable that the water absorbent resin is subjected to a thermal treatment. Conditions of the thermal treatment are: water absorbent resin precursor or a heating medium used to perform the thermal treatment preferably has a temperature in a range of 100° C. to 250° C., and more preferably in a range of 150° C. to 250° C.; and heating period in the thermal treatment is preferably in a range of one minute to two hours. Examples of appropriate combinations of the heating temperature and heating period are: (a) 180° C. for 0.1 to 1.5 hours, and (b) 200° C. for 0.1 to one hours.

Note that in case where the water absorbent resin precursor is prepared by the reverse phase suspension polymerization, it is possible to obtain a water absorbent resin, whose surface has been cross-linked, by dispersing the surface cross-linking agent in a hydrophobic organic solvent used in the reversed suspension polymerization, for example, in such a manner that the water-containing gel-form cross-linked polymer has a moisture content of not more than 50 mass %, preferably not more than 40 mass %, and more preferably not more than 30 mass %, during and/or after the azeotropical drying.

The water absorbent resin of the present invention that is obtained by performing the surface cross-linking treatment as required is granulated into particles having a particular particle size in order to have fluidity (anti-caking) at the time of moisture absorption and have so tolerance against mechanical shock that the mechanical shock will not cause significant deterioration in the water absorbent capability and the fluidity at the time of moisture absorption. Specifically, in the water absorbent resin of the present invention, it is preferable that, with respect to 100 mass % of the whole water absorbent resin contained in the particulate water absorbent, 90 to 100 mass % of the water absorbent resin has a particle diameter of less than 850 µm but not less than 106 µm, and 60 mass % or more of the water absorbent resin has a particle diameter of not less than 300 µm. It is more preferable that, with respect to 100 mass % of the whole water absorbent resin contained in the particulate water absorbent, 95 to 100 mass % of the water absorbent resin has a particle diameter of less than 850 µm but not less than 106 µm. It is particularly preferable that 98 to 100 mass % of the water absorbent resin has a particle diameter of less than 850 µm but not less than 106 µm. Moreover, it is more preferable that, with respect to 100 mass % of the whole water absorbent resin contained in the particulate water absorbent, 65 to 100 mass % of the water absorbent resin has a particle diameter of not less than 300 µm. It is further preferable that 70 to 100 mass % of the water absorbent resin has a particle diameter of not less than 300 µm. It is especially preferable that 75 to 100 mass % of the water absorbent resin has a particle diameter of not less than 300 µm.

Moreover, the water absorbent resin has a mass (weight) average particle diameter preferably of 200 µm to 700 µm, more preferably of 300 µm to 600 µm, further preferably of 400 µm to 500 µm. Further, as to the particle size distribution pf the water absorbent resin, it is preferable that a logarithmic standard deviation ($\sigma\zeta$ value) indicative of uniformity ranges from 0 to 0.40, more preferably from 0 to 0.35, most preferably from 0 to 0.30.

In case where a content of the water absorbent resin whose particle diameter is 850 µm or more exceeds 10 mass % with respect to 100 mass % of the whole water absorbent resin contained in the particulate water absorbent, the water absorbent resin gives foreign-substance feeling when used in a sanitary material such as a diaper, so that the user feels uncomfortable, for example, having rough feeling thereof. Moreover, in case where a content of the water absorbent resin whose particle diameter is less than 106 µm exceeds 10 mass % with respect to 100 mass % of the whole water absorbent resin contained in the particulate water absorbent, and in case where the logarithmic standard deviation $\sigma\zeta$ exceeds 0.40, there occur the following problems: the absorbency under pressure largely drops; the fluidity at the time of moisture absorption deteriorates; a working condition is deteriorated since dusts occur during producing the water absorbent resin and a sanitary material such as a diaper; segregation is increased due to a wider particle size distribution. Thus, the foregoing setting is not preferable.

[Organic Acid Multivalent Metal Salt]

Organic acid multivalent metal salts according to the present invention have seven or more carbons in its molecule and made from non-alkaline metal salts including fatty acids, petroleum acids, and polyacids.

Organic acids constituting the organic acid multivalent metal salts may be any organic substance which forms a salt with a multivalent metal. Preferable examples include organic carboxylic acids, organic sulfonic acids, and organic sulfinic acids. Particularly preferred among them are organic carboxylic acids with a carboxyl group in the molecule. The organic acid multivalent metal salt has seven or more carbons, preferably 7 to 20 carbons, and more preferably 12 to 20 carbons.

Using an organic acid with less than seven carbons in its molecule is not preferable, because the organic acid multivalent metal salt would exhibit a high solubility in water and when used in a paper diaper, absorber, etc. might liquate out into a liquid absorbed such as urine and blood. Besides, using oxalic acid, citric acid, or another acid with less than seven carbons in its molecule raises a potential issue of poor absorbent characteristics under mechanical shock because of high hardness of the organic acid multivalent metal salt produced. The use of oxalic acid is not preferably also for safety concerns.

The organic carboxylic acids are, for example, saturated or unsaturated organic carboxylic acids and aromatic carboxylic acids. The organic carboxylic acids may have substitution groups, other than carboxylic acids, for example, hydroxyl groups and halogens. Also, the organic carboxylic acids may contain two or more carboxyl groups per molecule. Further, the organic carboxylic acids may be multivalent carboxylic acids containing a plurality of carboxyl groups in each molecule, but it is preferable that the organic carboxylic acids are monocarboxylic acids.

Specifically, examples of the organic carboxylic acids include long chain and branched chain fatty acids, such as capronic acid, octanoic acid, octynoate, decanoic acid, lauryl acid, myristic acid, palmitic acid, oleic acid, and stearic acid; petroleum acids, such as benzoic acid, myristic acid, naphthenic acid, naphthoic acid, and naphthoxyacetic acid; and polyacids, such as poly(meth)acrylic acid and polysulfonic acid. Particularly preferred among these acids are fatty acids, such as capronic acid, octanoic acid, octynoate, decanoic acid, lauryl acid, myristic acid, palmitic acid, oleic acid, stearic acid, bovine fatty acid, and castor curing fatty acid; and fatty acids with no unsaturated bonds in molecules (long chain saturated fatty acid), such as capronic acid, octanoic acid, decanoic acid, lauric acid, myristic acid, palmitic acid, and stearic acid. The most preferred are long chain fatty acids with no unsaturated bonds in molecules (long chain saturated fatty acid) having 12 to 20 carbons, such as lauric acid, myristic acid, palmitic acid, and stearic acid. Fatty acids with unsaturated bonds in molecules are not preferred because the resultant particulate water absorbent might color, produce an odor, and develop other undesirable phenomena in heat or when oxidized in storage.

The metal salts constituting the organic acid multivalent metal salts are not limited in any particular manner: the metal salts may be any non-alkaline metal salt, such as alkaline earth metal salts and transition metal salts. Preferred for easy availability are barium salts, calcium salts, magnesium salts, aluminum salts, and zinc salts. Particularly preferred among these are calcium salts, magnesium salts, zinc salts, and aluminum salts.

Therefore, specific examples of the organic acid multivalent metal salts include calcium laurate, magnesium laurate, zinc laurate, aluminum laurate, calcium myristate, magnesium myristate, aluminum myristate, zinc myristate, calcium palmitate, magnesium palmitate, aluminum palmitate, zinc palmitate, calcium stearate, magnesium stearate, zinc stearate, and aluminum stearate.

Further, the organic acid multivalent metal salts may partly form a hydroxide or the like, or more specifically, have a salt structure represented by, for example, (Organic Acid)$_x$ M$^{n+}$(OH)$_{n-x}$, where M$^{n+}$ is a metal ionic species with a charge of +n, x is an integer from 1 to n, and n is 2 or a greater integer.

The organic acids and metal salts may make up the organic acid multivalent metal salts in any combination. One of the organic acid multivalent metal salts may be used alone, or two or more of them may be used in mixture.

The organic acid multivalent metal salts are not limited to those having all acid radicals neutralized, but may contain therein a small amount of an organic acid and/or an excessive amount of a multivalent metal. Preferred for use among them is a salt with 90 or more mole % of all acid radicals (carboxyl groups) being neutralized. The percentage is more preferably 95 mole % to 105 mole %, even more preferably 98 mole % to 102 mole %, and especially preferably 99 mole % to 101 mole %.

If the organic acid used is a polyacid like polyacrylic acid, the polyacid has preferably 95 or more mole % of all acid radicals (carboxyl groups) thereof being neutralized, forming a salt with the multivalent metal. The percentage is more preferably 98 or more mole %, and even more preferably 99 or more mole %. The polyacid used has a typical weight-average molecular weight of 10,000 to 5,000,000, preferably 50,000 to 1,000,000.

The organic acid multivalent metal salts are particulate and may have any particle diameter. Usually, the particle diameter is preferably smaller than the weight-average (mass-average) particle diameter of the water absorbent resin. Specifically, 90 or more mass % of the organic acid multivalent metal salt(s) in the particulate water absorbent according to the present invention has a particle diameter of more than 0 to 100 μm, preferably 0.01 to 50 μm, and more preferably 0.01 to 10 μm.

Further, the melting point of the organic acid multivalent metal salt preferably ranges from not less than 20° C. to not more than 250° C., more preferably from not less than 40° C. to not more than 250° C., and even more preferably from not less than 50° C. to not more than 250° C. In this range, especially preferred is the range from not less than 60° C. to not more than 250° C., more preferred is the range from not less than 70° C. to not more than 250° C., and the most preferred is the range from not less than 80° C. to not more than 250° C. If the melting point of the organic acid multivalent metal salt is 250° C. or above, the organic acid multivalent metal salt may not stick well to the surface of the water absorbent resin; an increased amount of the organic acid multivalent metal salt would possibly peel off from the water absorbent resin. Melting points equal to or below 20° C. are not desirable, because the produced particulate water absorbent has less fluidity and more difficult to handle.

That is, in industrial applications of the water absorbent, storage hoppers, transportation lines, metering feeders, etc. for the water absorbent are generally heated at 30 to 80° C. to prevent the water absorbent from absorbing moisture.

Typical conventional additives, such as polyethylene glycol and surfactants, which are used to improve the properties, especially fluidity, of powder at the time of moisture absorption or at a water content below 20 mass % have mostly a low melting point or a low glass transition temperature. These water absorbents may exhibit excellent fluidity at room temperature. Nevertheless, in high humidity in manufacturing equipment and transportation lines in the manufacture of water absorbents and diapers, for example, the additives melt, degrading the fluidity of the water absorbent powder and making it difficult to handle the water absorbent powder. In contrast, the present invention uses the organic acid multivalent metal salt with the foregoing melting point, and therefore does not create difficulty in handling the water absorbent in high humidity in industrial applications.

The melting point of the organic acid multivalent metal salt may be measured, or its value may be taken from a publication, e.g., Kagaku Dai Jiten (Encyclopedia of Chemical Technology, edited by Editing Committee for Encyclopedia of Chemical Technology, published by Kyoritsu Shuppan Co., Ltd). For example, zinc stearate has a melting point of 128 to 130° C., aluminum stearate of 103° C., calcium stearate of 180° C., and magnesium stearate of 200° C. These organic acid multivalent metal salts are preferably used because of their melting points which are optimal when used in the manufacture of the particulate water absorbent according to the present invention. Depending on the selection of the organic acid multivalent metal salt used, the melting point may be adjusted in a wide range. Note that in actual use, an organic acid multivalent metal salt is preferably selected which has a melting point higher than or equal to temperatures at which the particulate water absorbent according to the present invention is used.

It is preferable that the organic acid multivalent metal salt is hardly soluble or insoluble, for example, the organic acid multivalent metal salt has a solubility preferably from not less than 0 g/L to not more than 10 g/L in 1000 mL of deionized water at 25° C. The solubility is more preferably from not less than 0 g/L to not more than 5 g/L, and even more preferably from not less than 0 g/L to not more than 2 g/L. If the solubility of the organic acid multivalent metal salt exceeds 10 g/L, the organic acid multivalent metal salt may undesirably liquate out into a liquid absorbed, such as urine and blood, as mentioned earlier.

[Water Absorbent (Particulate Water Absorbent)]

<Production Method of Particulate Water Absorbent>

The particulate water absorbent according to the present invention should only have to have the unique parameters (detailed later), and preferably contains the aforementioned water absorbent resin and organic acid multivalent metal salt, and is produced by a method which is not limited in any particular manner. The water absorbent may be produced, for example, by one of methods 1 to 3 below. The water absorbent resin in the particulate water absorbent may be either a water absorbent resin whose surface has been cross-linked or a water absorbent resin precursor whose surface has not been cross-linked. The surface cross-linking water absorbent resin for use in the production of the particulate water absorbent may be obtained by adding a mixture of a surface cross-linking agent and an organic acid multivalent metal salt to a water absorbent resin precursor prepared in advance. Alternatively, an organic acid multivalent metal salt may be mixed with a surface cross-linking water absorbent resin prepared in advance.

The particulate water absorbent according to the present invention produced by one of these methods as examples has unique parameters such as mass-average particle diameter, quantity of soluble component, fluidity index at the time of moisture absorption (moisture absorption fluidity index), moisture absorption fluidity retention index, absorbency under pressure, absorbency-under-pressure retention index, maximum insertion load, insertion work, and recovery index. Details will be given later.

(Method 1)

An organic acid multivalent metal salt is dispersed in a monomer solution, containing an internal cross-linking agent, which is used to polymerize an unsaturated monomer, thereby polymerizing the unsaturated monomer. The product is dried and crushed where necessary to prepare a water absorbent resin precursor. A surface of the precursor is then cross-linked to obtain a particulate water absorbent according to the present invention.

(Method 2)

An organic acid multivalent metal salt is added and mixed with a water absorbent resin precursor. A surface of the water absorbent resin precursor is cross-linked to obtain a particulate water absorbent.

(Method 3)

A surface of a water absorbent resin precursor is cross-linked to prepare a surface cross-linking water absorbent resin to which an organic acid multivalent metal salt is then added and mixed to obtain a particulate water absorbent.

A monomer may be added during the polymerization of an unsaturated monomer as in method 1. Methods 2 and 3 offer preferred alternatives to this, where an organic acid multivalent metal salt is added to a water absorbent resin precursor or surface cross-linking water absorbent resin so that the organic acid multivalent metal salt evenly adheres to the surface of the water absorbent resin. The alternatives provide a particulate water absorbent according to the present invention which better fulfills its purposes. In other words, the organic acid multivalent metal salt is preferably added when cross-linking a surface of the water absorbent resin precursor or to the water absorbent resin whose surface has been cross-linked.

Generally provided in powder form, the organic acid multivalent metal salt can be mixed with a water absorbent resin by, for example, one of the methods: (i) dry blending whereby the organic acid multivalent metal salt in powder form is directly mixed with the water absorbent resin, (ii) dispersing the organic acid multivalent metal salt to form a slurry in the surface cross-linking solution which is a mixture of (a) the aforementioned surface cross-linking agent used in cross-linking the surface and (b) water and/or a hydrophilic organic solvent, in order to mix the organic acid multivalent metal salt with the water absorbent resin precursor, and (iii) dispersing the organic acid multivalent metal salt to form a slurry in water and/or a hydrophilic organic solvent to mix the organic acid multivalent metal salt with the water absorbent resin.

In mixing the organic acid multivalent metal salt with the water absorbent resin by dispersing the organic acid multivalent metal salt to form a slurry as in (ii) and (iii), the dispersion solvent composed of water and/or a hydrophilic organic solvent is added at quantities which differ depending on the type and particle size (particle diameter) of water absorbent resin. For example, when the dispersion solvent is water, the dispersion solvent is normally added at not more than 10 parts by mass, preferably from 1 to 5 parts by mass, to every 100 parts by mass of solid content in the water absorbent resin. When the dispersion solvent is a hydrophilic organic solvent, the dispersion solvent is normally added at not more than 10 parts by mass, preferably 0.1 to 5 parts by mass, to every 100 parts by mass of solid content in the water absorbent resin.

Further, the organic acid multivalent metal salt is dispersed in the dispersion solvent to a concentration selected in accordance with the type of organic acid multivalent metal salt used, type of dispersion solvent, and viscosity of the slurry formed. Although not limited in any particular manner, the concentration is normally from 0.001 to 30 mass %, preferably from 0.01 to 10 mass %, to the combined mass of the organic acid multivalent metal salt and dispersion solvent. The water absorbent resin (powder) may be mixed with the organic acid multivalent metal salt at room temperature or higher. To impart water absorption characteristics and fluidity at the time of moisture absorption to the particulate water absorbent, the temperature is typically 40° C. or higher, preferably 40 to 300° C., more preferably 50 to 250° C., and even more preferably 60 to 250° C.

The particulate water absorbent according to the present invention contains the organic acid multivalent metal salt at quantities which differ depending on the fluidity at the time of moisture absorption and absorbent characteristics required with the resultant particulate water absorbent. The organic acid multivalent metal salt contained is preferably from more than 0 parts by mass to less than 10 parts by mass, more preferably from not less than 0.001 parts by mass to less than 10 parts by mass, even more preferably from not less than 0.001 parts by mass to not more than 7 parts by mass, yet more preferably from not less than 0.01 parts by mass to not more than 5 parts by mass, and most preferably from not less than 0.01 parts by mass to not more than 3 parts by mass, to every 100 parts by mass of solid content in the water absorbent resin. Particularly preferred in these ranges is from not less than 0.05 parts by mass to not more than 1 part by mass. If the organic acid multivalent metal salt accounts for 10 parts by weight or more, the resultant fluidity at the time of moisture absorption and alleviation of water absorptive capacity degradation under mechanical shock are far lower than levels expected from that content and therefore uneconomical. Besides, the excessive content possibly reduces water absorptive capacity.

Any ordinary mixer can be used to mix the water absorbent resin with the organic acid multivalent metal salt. Examples include cylindrical mixers, screw mixers, screw extruders, turbulizers, nauta mixers, V-shaped mixers, ribbon blenders, double-arm kneaders, flow mixers, air current mixers, rotary disc mixers, roll mixers, and convolution mixers. The mixing rate is of any value.

<Other Components of Particulate Water Absorbent>

To acquire various capabilities, the particulate water absorbent according to the present invention may contain substances other than those mentioned so far (water absorbent resin, organic acid multivalent metal salt, internal cross-linking agent, polymerization initiator, surface cross-linking agent, etc.). These additional substances may be insoluble fine particles such as inorganic powder and hydrophilic solvents such as water, to granulate the water absorbent resin, for example.

Specific examples of the inorganic powder include metal oxides, such as silicon dioxide and titanium oxides; silicic acids (salts), such as natural zeolite and synthetic zeolite; kaolin; talc; clays; and bentonite. Preferred among them are silicon dioxide and silicic acids (salts), particularly silicon dioxide and silicic acids (salts) having an average particle diameter of 200 µm or less as measured using a Coulter counter.

The inorganic powder may be added at quantities which differ depending on the combination of the various components and inorganic powder in the particulate water absorbent. The inorganic powder content is preferably from 0 to 6 parts by mass, preferably from 0.001 to 5 parts by mass, and more preferably from 0.01 to 3 parts by mass, in every 100 parts by mass of the water absorbent resin. An inorganic powder content beyond these ranges may be in excess of the shock absorptive capability provided by the organic acid multivalent metal salt; it could be difficult to prevent degradation of shock force absorbing properties.

The inorganic powder may be mixed with the water absorbent resin by any method. An example is dry blending or wet blending whereby two kinds of powder is mixed together, of which dry blending is more desirable.

To acquire various functions, the particulate water absorbent according to the present invention may be, where necessary, subjected to another step of adding various additives. Examples of the additives include a deodorant, antibacterial agent, perfume, foaming agent, pigment, dye, plasticizer, adhesive, surfactant, fertilizer, oxidizing agent, reducing agent, water, salt, chelating agent, bactericide, hydrophilic macro molecules, such as polyethylene glycol, and polyethyleneimine, hydrophobic macro molecules, such as paraffin, thermoplastic resins, such as polyethylene and polypropylene, and heat curing resins, such as a polyester resin and urea resin. The additives are added at quantities from 0 to 30 parts by mass, preferably from 0 to 10 parts by mass, more preferably 0 to 1 part by mass, to every 100 parts by mass of the water absorbent resin.

<Particle Diameters of Particulate Water Absorbent>

The particulate water absorbent according to the present invention contains, as described above, the water absorbent resin, organic acid multivalent metal salt, and other components, and where necessary, is granulated using water-insoluble fine particles or a hydrophilic solvent and the like. Preferably, particles from not less than 106 µm to less than 850 µm account for from not less than 90 mass % to not more than 100 mass % of the particulate water absorbent. More preferably, those particles account for from not less than 95 mass % to not more than 100 mass % of the particulate water absorbent. Even more preferably, those particles account for from not less than 98 mass % to not more than 100 mass % of the particulate water absorbent. A granulation, if at all, is preferably carried out so that the particulate water absorbent has these specific particle diameters.

If more than 10 mass % of the particulate water absorbent is made up of particles less than 106 µm, an aqueous solution such as blood and urine does not diffuse well in the absorber prepared from, among others, fiber base material and the particulate water absorbent used as an absorbent article absorbing an aqueous solution. In addition, the surface area increases where the particulate water absorbent comes in contact with air, which undesirably makes the particulate water absorbent more likely to dissolve. In contrast, if more than 10 mass % of the particulate water absorbent is made up of particles greater than 850 µm, the particulate water absorbent have a reduced absorption rate and when worn as an absorbent article, gives an undesirable uncomfortable, foreign feel on the skin.

<Quantity of Water Soluble Content (Soluble Content) in Particulate Water Absorbent>

The quantity of water soluble content (soluble content) in the particulate water absorbent according to the present invention is preferably from 0 to 30 mass %, more preferably from 0 to 25 mass %, even more preferably from 0 to 20 mass %, and yet more preferably from 0 to 15 mass % to the mass of the particulate water absorbent. The most preferable range is from 0 to 10 mass %. If the soluble content exceeds this range, the soluble content liquates out into the absorber when the particulate water absorbent used as an absorbent article has absorbed water. This may interrupt diffusion of blood, urine, etc. in the absorber, which is undesirable.

<Absorbency Under Pressure of Particulate Water Absorbent>

The particulate water absorbent according to the present invention has an absorbency under a 2.06 kPa and/or 4.83 kPa pressure (load) of 15 g/g or greater, preferably 18 g/g or greater, more preferably 20 g/g or greater, even more preferably 23 g/g or greater, and most preferably 25 g/g or greater. The maximum value of the absorbency under pressure is not limited in any particular manner; the greater the better. Considering the trade off with production cost and other factors, the maximum value is not more than 50 g/g, preferably not more than 45 g/g.

The absorbency under pressure is evaluated here under the load of 2.06 kPa and 4.83 kPa, based on an assumption that the particulate water absorbent according to the present invention is used in paper diapers and other sanitary materials receiving a load from an infant in a lying or sitting position.

The absorbency under pressure of the particulate water absorbent according to the present invention decreases little when a shock force is applied to the particulate water absorbent. Therefore, the particulate water absorbent prevents absorption characteristics from being degraded by mechanical destruction in the manufacture of the particulate water absorbent. The water absorbent capacity and fluidity at the time of moisture absorption does not decrease by a large amount when the particulate water absorbent is under mechanical shock in the course of the production of absorbent articles.

The absorbency under pressure of the particulate water absorbent under the shock force is evaluated by an absorbency-under-pressure retention index. The absorbency-under-pressure retention index indicates a change in the absorbency under pressure of the particulate water absorbent before and after applying a shock force. Details will be given later in reference to application examples. The absorbency-under-pressure retention index of the particulate water absorbent according to the present invention is preferably 0.90 or greater, more preferably 0.95 to 1.10, and even more preferably 0.95 to 1.00.

As discussed in the foregoing, the particulate water absorbent according to the present invention changes little in absorbent characteristics under a mechanical shock. It therefore becomes possible to accurately predict and manage the absorption characteristics of diapers and other produced absorbent articles. Besides, unlike conventional cases, the absorbent characteristics do not deteriorate during the production of absorbent articles despite high absorbent capacity of the water absorbent resin. Therefore, neither the absorbent capacity of the absorbent article nor the amount of the particulate water absorbent used in an absorbent article to achieve consistent quality does not need to be increased over design levels. This enables the amount of the particulate water absorbent used in the production of the absorbent article to be reduced.

<Fluidity (Anti-caking) of Particulate Water Absorbent at the Time of Moisture Absorption>

The moisture-absorption fluidity (fluidity at the time of moisture absorption) of the particulate water absorbent according to the present invention is evaluated by the fluidity measured on the particulate water absorbent in the form of blocks, cakes, and powder which is let rest at 25° C. and a relative humidity of 90% RH. The particulate water absorbent according to the present invention contains about 10 to 30 mass % water. A water content ratio of 15 to 30 mass % does not cause the powder to block or cake and results in excellent moisture-absorption fluidity.

The fluidity index (an amount of particles passing through a sieve, described later), of the particulate water absorbent according to the present invention, by which the moisture-absorption fluidity is evaluated is from not less than 90 mass % to not more than 100 mass %, preferably not less than 95 mass % to not more than 100 mass %, and more preferably not less than 98 mass % to not more than 100 mass %.

The moisture-absorption fluidity of the particulate water absorbent under a shock force is evaluated by a moisture absorption fluidity retention index. The moisture absorption fluidity retention index indicates a change in the moisture-absorption fluidity of the particulate water absorbent before and after the application of a shock force. The particulate water absorbent according to the present invention has a moisture absorption fluidity retention index of 0.90 or greater, preferably from 0.95 to 1.10, and more preferably from 0.97 to 1.10, and particularly preferably from 0.97 to 1.00. The particulate water absorbent, after the application of a shock force, does not have the fluidity at the time of moisture absorption reduced and retains good, stable moisture-absorption fluidity. The fluidity index and the moisture absorption fluidity retention index will be detailed later in reference to application examples.

Therefore, decreases in the moisture-absorbed fluidity and related amassing and blocking of the particles in the particulate water absorbent are prevented under a mechanical shock in an absorbent article production process. This prevents from the powder from clogging the production apparatus and making the apparatus inoperative.

<Shape of Particulate Water Absorbent>

General examples of the shape of the water absorbent include the primary particles shape, from spherical and ellipsoidal to partially flattened ellipsoidal, obtained by reverse phase suspension polymerization illustrated in U.S. Pat. No. 5,244,735, FIGS. 1, 2; the shape of a granulated product of the primary particles produced by agglomeration of spherical and/or ellipsoidal particles, like agglomerated beads illustrated in NON WOVENS WORLD, October–November 2000 Issue (published by Marketing Technology Service, Inc.), page 75, FIG. 1; and the indefinite shapes of a crushed product of a water-containing gel-like polymer obtained by polymerization of an aqueous monomer solution and the shapes of the granulated product of the crushed product, like crystals in U.S. Pat. No. 5,981,070, FIGS. 2, 3, 4 and NON WOVENS WORLD, October–November 2000 Issue, page 75, FIG. 1.

The particulate water absorbent according to the present invention is preferably of a shape other than the shape of spherical primary particles and the shape of ellipsoidal primary particles, more preferably of a shape of the granulated product of spherical or ellipsoidal particles, of an indefinite shape of a crushed product of a water-containing gel-like polymer obtained by polymerization of an aqueous monomer solution, or of a shape of the granulation product of the crushed product, and even more preferably of an indefinite shape or a shape of the granulation product.

The non-preference for spherical primary particles and/or ellipsoidal primary particles is because the shapes do not mix well with pulp and other fiber materials in, for example, the production of absorbent articles, and the particulate water absorbent is easy to fall from an absorber based on a mixture of the particulate water absorbent and a fiber material. Therefore, the use of the water absorbent in the form of spherical primary particles and/or ellipsoidal primary particles raises a problem that it becomes difficult to uniformly distribute the water absorbent in an absorber.

<Powder Characteristics of Particulate Water Absorbent>

The particulate water absorbent according to the present invention is not sticky, shows a low internal friction coefficient or internal friction angle, and hence a small repose angle, and exhibits excellent fluidity in powder form, not only at the time of moisture absorption and in the gelatinous state but also in a dry state where the water content is 0 to 20 mass %, further, 0 to 10 mass %. The internal friction coefficient and the internal friction angle are measured by a shear test of a powder layer. A powder shear test can be carried out using a device of a shear box, ring shear, or parallel plate type. An example is a Jenike Shear cell.

Typical spherical primary particles and/or ellipsoidal primary particles prepared by reverse phase suspension polymerization are known to show high fluidity. Meanwhile, particles of shapes generally described as "indefinite" and of shapes other than the shapes of spherical primary particles and the shapes of ellipsoidal primary particles have a high internal friction coefficient, hence extremely low fluidity, due to the distortion of the particles. The primary particles are, for example, of indefinite crushed shapes of particles manufactured by aqueous solution polymerization. Even in the case of the particles prepared by reverse phase suspension polymerization, particles obtained by the granulation of the spherical primary particles and/or ellipsoidal primary particles have a high internal friction coefficient, hence extremely low fluidity, due to the distortion of the particles.

Therefore, a water absorbent made up of particles with a high internal friction coefficient has increased transportation resistance in air flow transportation, in transportation using a paddle-type transporter, and in transportation using a screw-type transporter. In other words, when handling "indefinite" particles having shapes other than the shapes of spherical primary particles and the shapes of ellipsoidal primary particles, conventional water absorbents clog production apparatus and transportation devices. The clogging results in a problem of excessive load, frequently halting their operation.

Conventionally, to secure fluidity in a moisture absorbing environment, an inorganic substance is generally added to the water absorbent. The addition of a inorganic substance to the water absorbent degrades fluidity, especially, in a dry state where the water content ratio is 0 to 20 mass %. The water absorbent frequently clogs production apparatus and transportation devices, which causes excessive load and halts their operation.

However, the particulate water absorbent according to the present invention, since containing the aforementioned water absorbent resin and organic acid multivalent metal salt, exhibits extremely high fluidity in the form of compacted powder (hereinafter, "powder fluidity") even when the powder is a particle having a shape other than a shape of a spherical primary particle and a shape of an ellipsoidal primary particle.

Accordingly, the inventors of the present invention evaluated the powder fluidity of the particulate water absorbent, and if the evaluation indicated a predetermined powder fluidity, regarded that the particulate water absorbent has excellent powder fluidity and is extremely easy to handle by production apparatus and transportation devices even when the particulate water absorbent is constituted of a particle having a shape other than a shape of a spherical primary particle and a shape of an ellipsoidal primary particle. The inventors then evaluated, based on this assumption, the powder fluidity of the particulate water absorbent by the following two evaluation methods.

A first powder fluidity evaluation method is carried out in this manner: A probe (metal rod), an insertion member, is vertically inserted to 20 mm deep in a particulate water absorbent in a compacted state. The powder fluidity is evaluated by a maximum insertion load (probe insertion load by 20 mm insertion, or "PIL") and an insertion work (probe insertion work by 20 mm insertion, or "PIW") with the probe inserted to 20 mm deep. According to the first evaluation method, less PIL values with the probe inserted to 20 mm deep and less PIW values with the probe inserted to 20 mm deep indicate that the particulate water absorbent in powder form has a lower internal friction coefficient and frictional force and higher sliding properties.

Many conventionally known water absorbent resins and water absorbents in powder form have high frictional force and do not even allow the 20-mm deep probe insertion distance (probe insertion distance, or "PID," in accordance with the present invention).

In contrast, the particulate water absorbent according to the present invention is indefinite-shaped particles having shapes other than shapes of spherical primary particles and shapes of ellipsoidal primary particles, and has a low PIL when the probe is inserted 20 mm. Specifically, the PIL is from not less than 0 g-weight to not more than 5000 g-weight, preferably from not less than 0 g-weight to not more than 3000 g-weight, more preferably from not less than 0 g-weight to not more than 2000 g-weight, even more preferably from not less than 0 g-weight to not more than 1000 g-weight. Especially preferred among these ranges is from not less than 0 g-weight to not more than 900 g-weight, more preferably from not less than 0 g-weight to not more than 700 g-weight, and most preferably from not less than 0 g-weight to not more than 500 g-weight.

The PIW of the particulate water absorbent according to the present invention when the probe is inserted 20 mm is from not less than 0 g-weight×mm to not more than 50,000 g-weight×mm, preferably from not less than 0 g-weight×mm to not more than 30,000 g-weight×mm, more preferably from not less than 0 g-weight×mm to not more than 10,000 g-weight×mm, even more preferably from not less than 0 g-weight×mm to not more than 8,000 g-weight×mm, and still more preferably from not less than 0 g-weight×mm to not more than 7,000 g-weight×mm. Especially preferred among these ranges is from not less than 0 g-weight×mm to not more than 6, 500 g-weight×mm, and more preferably from not less than 0 g-weight×mm to not more than 6,000 g-weight×mm, and most preferably from not less than 0 g-weight×mm to not more than 5,000 g-weight×mm. If the PIW exceeds these ranges, the particulate water absorbent has a great internal friction coefficient and frictional force, making it difficult to produce a water absorbent with excellent powder fluidity.

A second powder fluidity evaluation method is carried out in this manner: A probe (metal rod) is inserted to 20 mm deep in a particulate water absorbent in a compacted state twice without an interval. An evaluation is made on the basis of a ratio of the insertion work in the second insertion (reinsertion work) to the insertion work in the first insertion. The ratio is defined as a recovery index when the probe is inserted 20 mm (recovery index by 20 mm insertion, or "RI"). According to the second evaluation method, greater RI values (nearer to 100%) indicate that the particulate water absorbent has a greater powder fluidity and a smaller force sticking particles together.

The particulate water absorbent obtained from the present invention is indefinite-shaped particles having shapes other than shapes of spherical primary particles and shapes of ellipsoidal primary particles, and has an RI, with the probe inserted 20 mm, of 55% or greater, preferably 60% or greater, and more preferably from not less than 65% to not more than 100%. Especially preferred among these ranges is from not less than 60% to not more than 100%, and most preferably, from not less than 75% to not more than 100%.

As to the aforementioned powder fluidity, PIL, PIW, and RI do not exceed the aforementioned ranges in a temperature range of preferably from 0 to 100° C., more preferably from 30 to 80° C., even preferably from 50 to 80° C. Especially preferred among them is preferably from 60 to 80° C., most preferably from 70 to 80° C. Further, in the particulate water absorbent of the present invention, PIL, PIW, and RI have values within the aforementioned ranges without lowering the powder fluidity even after receiving the shock force.

These two powder fluidity evaluation methods proposed by the inventors of the present invention are excellent techniques capable of distinguishing powder fluidity clearer and more detailed than conventional powder evaluation methods based on flow rate, repose angle, etc. Therefore, by using one of the foregoing evaluation methods according to the present invention in the evaluation of the particulate water absorbent, a particulate water absorbent can be selected which exhibits extremely high fluidity which achieves a low PIL, a low PIW, and a high RI. The PIL, PIW, PID, and RI will be detailed further in terms of their calculation methods in reference to application examples.

As described above, by using the first and/or second powder fluidity evaluation method in the selection of a particulate water absorbent with a predetermined powder fluidity, it is possible to surely provide powder of the particulate water absorbent which has an improved powder fluidity. This allows, for example, reduced transportation resistance in air flow transportation of the particulate water absorbent, in transportation using a paddle-type transporter, and in transportation using a screw-type transporter. Conventionally frequent clogging of production apparatus and transportation devices, and halting of the devices due to overloading are all prevented.

Further, the organic acid multivalent metal salt in the particulate water absorbent obtained from the present invention has a high melting point. The particulate water absorbent can therefore be heated at a certain constant temperature as described above, and still exhibits powder fluidity which differs little from the powder fluidity at room temperature.

As described above, the particulate water absorbent according to the present invention exhibits both improved fluidity at the time of moisture absorption and improved fluidity in powder form, and also has very high fluidity. Besides, the particulate water absorbent according to the present invention has great powder fluidity in a dry state, thereby being capable of alleviating mechanical damage and hence reducing decrease in the absorbency under pressure and moisture-absorption fluidity due to mechanical damage.

Therefore, the particulate water absorbent according to the present invention has, as described above, excellent powder fluidity; the particulate water absorbent is useful in the facilitation of hoppers, powder storages, and like apparatus which are used in, for example, a production process of an absorber based on the particulate water absorbent.

[Absorber, Absorbent Article]

The particulate water absorbent according to the present invention is used for water absorbing purposes. It is widely used in the form of absorbers and absorbent articles, and preferably as sanitary materials to absorb urine, blood, and other body fluids. The absorber and absorbent article according to the present invention contains the particulate water absorbent according to the present invention.

The absorber here refers to an absorptive material prepared by molding the water absorbent resin and a hydrophilic fiber as main components. The absorber contains the particulate water absorbent at an amount (core concentration) of preferably from 20 to 100 mass %, and more preferably from 30 to 100 mass % to the combined mass of the water absorbent and the hydrophilic fiber. Especially preferred is the range from 40 to 100 mass %. The greater core concentration the particulate water absorbent according to the present invention has, the more distinct the effect of decreasing absorption characteristics of the particulate water absorbent when absorbers or absorbent articles are produced.

In addition, the absorbent article is made up of the absorber, a front sheet permeable to liquid, and a back sheet impermeable to liquid. The absorbent article, including paper diapers for adults and sanitary napkins, are produced in the following manner: First, the particulate water absorbent is blended or sandwiched with a fiber base material, for example, a hydrophilic fiber, to form an absorber (absorption core). The absorption core is then sandwiched between a liquid-permeable front sheet and a liquid-impermeable back sheet. Thereafter, an elasticity member, a diffusion layer, and/or adhesive tape is fitted if necessary. Under these conditions, the absorption core is compression molded to a density of 0.06 to 0.50 g/cm$^3$ and a basic weight of 0.01 to 0.20 g/cm$^2$. The fiber base material used is, for example, crushed wood pulp or a like hydrophilic fiber, a cotton linter, a cross-linked cellulose fiber, rayon, cotton, wool, acetate, or vinylon. These fiber base materials are preferably aerated.

EXAMPLES

Through the following examples and comparative examples, the present invention is described more specifically. However, the present invention is not limited to the following examples and the like, as long as the present invention is interpreted in light of a gist thereof. Note that, an absorbency without pressure, an absorbency under pressure, a weight (mass) average particle diameter, a fluidity index at the time of moisture absorption, a shock, a moisture absorption fluidity retention index, an absorbency-under-pressure retention index, a water-soluble component amount (soluble amount), a solid content ratio, a moisture content, a return amount, a diffusion ratio, a maximum insertion load, an insertion work, an insertion distance, and a recovery index were measured as described below.

Also note that, unless otherwise stated, "part(s)" means part(s) by mass (part(s) by weight). Further, in measuring the aforementioned parameters of the water absorbent or the water absorbent resin described later, the measurement was performed by using the water absorbent or the water absorbent resin generally without any modification. However, in case where the water absorbent or the water absorbent resin excessively absorbed moisture, that is, in case of a water absorbent or a water absorbent resin taken from an absorbent article such as a diaper, the measurement was performed after the following steps: the water absorbent or the water absorbent resin was dried as required under reduced pressure or in a similar manner so that it had a constant mass at 60° C. for example, and its moisture content adjusted to not more than 7±1 mass %, more preferably not more than 5±1 mass %.

[Absorbency Without Pressure (Absorbency (GV, Gel Volume) in 60 Minutes Under No Applied Pressure, with Respect to a 0.90 Mass % of Sodium Chloride Solution]

0.2 g of a particulate water absorbent resin (or a water absorbent) was evenly contained in a bag (60 mm×60 mm) made of a nonwoven fabric. Then, the bag was soaked in an extremely excessive amount (not less than 100 g for example) of 0.9 mass % sodium chloride solution (physiological saline) whose temperature had been adjusted to 25° C., and was withdrawn 60 minutes later. By using a centrifugal separator, the bag was drained for three minutes at 250 G, and a weight W2 (g) of the bag was measured.

Next, the same operation was performed without using the water absorbent and the water absorbent resin, and a weight W1 (g) was measured. Then, from the weights W1 and W2, an absorbency without pressure (g/g) was calculated according to the following (Equation 4).

Absorbency without pressure (g/g)=(weight $W2$ (g)−weight $W1$ (g))/weight of water absorbent or water absorbent resin (g)　　(Equation 4)

[Absorbency Under Pressure (Absorbency at which 0.90 Mass % of Sodium Chloride Solution was Absorbed for 60 Minutes Under Pressure of 2.06 kPa (AAP1))]

On a bottom of a plastic supporting cylinder having a 60 mm internal diameter, a stainless-steel 400 mesh (mesh size of 38 μm) was fusion-bonded. Then, under a condition of a room temperature (20° C. to 25° C.) and 50% RH relative humidity, 0.90 g of water absorbent or water absorbent resin was evenly dispersed on the mesh. Subsequently, a piston and a load are placed in this order on the water absorbent resin or the water absorbent. The piston is so adjusted as to evenly apply a 2.06 kPa (0.3 psi) load onto the water absorbent resin or the water absorbent. An external diameter of the piston is slightly smaller than 60 mm, so that there is no gap between the piston and the supporting cylinder, and upward and downward movements of the piston will not be hampered. Then, a weight Wa (g) of this measurement set was measured. Inside a petri dish having a 150 mm diameter, a glass filter (product of Sougo Rikagaku Glass Seisakusho Co., Ltd.; diameter of fine pores: 100 µm to 120 µm) having a 90 mm diameter was placed. Thereafter, a 0.90 mass % of sodium chloride solution (20° C. to 25° C.) was added until it reaches a level of an upper surface of the glass filter.

Then, a piece of filter paper (product of Advantec Toyo Kaisha, Ltd.; product name: JIS P3801, No. 2; thickness: 0.26 mm; diameter of retained particles: 5 µm) was placed thereon, so that an entire surface of the filter paper was wetted. An excess of the liquid was removed.

The measuring apparatus set was placed on the wet filter paper, so that the liquid was absorbed under the load. One hour (60 minutes) later, the measuring apparatus set was lifted, and a weight Wb (g) thereof was measured. From the weights Wa and Wb, an absorbency under pressure AAP1 (g/g) was calculated according to the following (Equation 5).

Absorbency under pressure $AAP1$ (g/g)=($Wb$ (g)–$Wa$ (g))/mass (0.9) g of water absorbent resin or water absorbent) (Equation 5)

[Absorbency Under Pressure (Absorbency at which 0.90 Mass % of Sodium Chloride Solution is Absorbed for 60 Minutes Under Pressure of 4.83 kPa (AAP2))]

Except that the 2.06 kPa load exerted to the water absorbent resin or the water absorbency was changed to a 4.83 kPa load (0.7 psi), the same operation as in the aforementioned calculation of AAP1 was performed, and an absorbency under pressure AAP2 (g/g) was calculated according to the following (Equation 6).

Absorbency under pressure $AAP2$ (g/g)=($Wb$ (g)–$Wa$ (g))/mass(0.9) g of a water absorbent resin or a water absorbent) (Equation 6)

[Weight (Mass) Average Particle Diameter]

A water absorbent or a water absorbent resin was sieved by using a JIS standard sieve of 850 µm, 710 µm, 600 µm, 500 µm, 425 µm, 300 µm, 212 µm, 150 µm, 106 µm, 75 µm, or the like, and a percentage is plotted on logarithmic probability paper. Further, in accordance with an aperture corresponding to R=50%, a weight average particle diameter (D50) was found.

Further, as to the particle size distribution, a logarithmic standard deviation σζ represented by the following (Equation 7) as an index. Here, as σζ approaches to 0, the particle size distribution is narrower.

$$\sigma\zeta = \frac{1}{2} \ln(X2/X1)$$ (Equation 7), where X1 represents a particle diameter when R=84.1%, and X2 represents a particle diameter when R=15.9%.

The sieving was performed as follows. Under a condition of a room temperature (20° C. to 25° C.) and 50% RH relative humidity, 10 g of the water absorbent resin powder or the water absorbent was put through a JIS standard sieve (The IIDA TESTING SIEVE; internal diameter: 80 mm) of 850 µm, 710 µm, 600 µm, 500 µm, 425 µm, 300 µm, 212 µm, 150 µm, 106 µm, 75 µm, or the like, and was classified for 10 minutes by using a low-tap-type sieve shaking apparatus (ES-65 sieve shaking apparatus, product of Iida Seisakusho, Ltd.). Note that the weight average particle diameter (D50) is measured in accordance with U.S. Pat. No. 5,051,259.

[Moisture Absorption Fluidity Index (Anti-caking at the Time of Moisture Absorption)]

Approximately 2 g of water absorbent resin or a water absorbent was evenly dispersed into an aluminum cup having a diameter of 52 mm, and was left for one hour in a constant-temperature-and-moisture apparatus (PLATINOUS LUCIFFER PL-2 G, product of TABAI ESPEC CORPORATION) at 25° C. and 90±5% RH relative humidity. One hour later, the water absorbent or the water absorbent resin in the aluminum cup was softly moved onto a JIS standard sieve (The IIDA TESTING SIEVE; internal diameter: 80 mm) of JIS 8.6 mesh (mesh size of 2000 µm), and was classified for 5 seconds by using a low-tap-type sieve shaking apparatus (ES-65 sieve shaking apparatus, product of Iida Seisakusho, Ltd.; rotational frequency: 230 rpm; shock frequency: 130 rpm.), under a condition of a room temperature (20° C. to 25° C.) and 50% RH relative humidity. Then, a weight (i (g)) of the water absorbent or the water absorbent resin which remained on the 2000 µm mesh and a weight (j (g)) of the water absorbent or the water absorbent resin which passed through the mesh were measured. Further, a moisture-absorption-fluidity index which is an index of fluidity at the time of moisture absorption was calculated according to (Equation 8). Note that, the moisture-absorption-fluidity index is defined by the following (Equation 8).

Moisture-absorption-fluidity index (% by weight)=(($j$ (g))/($i$ (g)+$j$ (g)))×100 (Equation 8)

[Shock]

As a method of applying the shock to a water absorbent or a water absorbent resin, the method described in Japanese Publication for Unexamined Patent Application, Tokukaihei 9-235378, page 7, [0049] to [0053], or the method described in U.S. Pat. No. 6,071,976, column 7, line 60, to column 8, line 26 was used, so as to apply the shock B described in the publications to a water absorbent or a water absorbent resin.

That is, first, 30.0 g of a water absorbent or a water absorbent resin, and 10.0 g of glass beads having a 6 mm diameter were placed in a container (product name: A-29, a mayonnaise bottle produced by Yamamura Glass Co., Ltd.; see U.S. Pat. No. 6,071,976, FIG. 12, container 41) having a 125 mL internal volume. The container was then sealed, and then mounted to a dispersing apparatus (No. 488 Testing Dispersing Apparatus, product of Toyo Seiki Seisakusho, Ltd.; U.S. Pat. No. 6,071,976, FIG. 14). By using the dispersing apparatus, the container was vibrated for 30 minutes at a vibration speed rotational frequency of 750 rpm under a condition of 100V/60 Hz, thereby applying the shock to the water absorbent or the water absorbent resin.

[Moisture Absorption Fluidity Retention Index]

A moisture absorption fluidity retention index is a ratio indicative of a moisture absorption fluidity index before and after applying the shock to the water absorbent or the water absorbent resin, and the moisture absorption fluidity index of the water absorbent or the water absorbent resin was calculated in accordance with the aforementioned (Equation 8) before and after applying the shock, and the moisture absorption fluidity retention index was calculated from thus calculated moisture absorption fluidity index in accordance with the following (Equation 1).

Moisture absorption fluidity retention index=$Y/X$ (Equation 1), where X is a moisture absorption fluidity index before the shock was applied, and Y is a moisture absorption fluidity index after the shock was applied.

[Absorbency-Under-Pressure-Retention Index]

An absorbency-under-pressure-retention index is a ratio indicative of an absorbency under pressure before and after applying the shock to the water absorbent or the water absorbent resin. Specifically, absorbencies under pressure AAP1 and AAP2 of the water absorbent or the water absorbent resin were respectively measured before and after applying the shock, and absorbency-under-pressure-retention indexes thereof were respectively calculated under the 2.06 kPa load and the 4.83 kPa load in accordance with the following (Equation 2) and (Equation 3). Note that, hereinafter, an absorbency-under-pressure-retention index under the 2.06 kPa load is defined as a first absorbency-under-pressure-retention index, and an absorbency-under-pressure-retention index under the 4.83 kPa load is defined as a second absorbency-under-pressure-retention index.

First Absorbency-under-pressure-retention index=$Q1/P1$ (Equation 2), where P1 is an absorbency under pressure under the 2.06 kPa load before a predetermined shock was applied, and Q1 is an absorbency under pressure under the 2.06 kPa load after a predetermined shock was applied.

Absorbency under pressure retention index $2 = Q2/P2$ (Equation 3), where P2 is an absorbency under pressure under the 4.83 kPa load before a predetermined shock was applied, and Q2 is an absorbency under pressure under the 4.83 kPa load after a predetermined shock was applied.

[Quantity of Water Soluble Component (Quantity of Soluble Component)]

184.3 g of a 0.90 mass % of sodium chloride solution was measured and pored into a 250 ml plastic container having a cover. Into the solution, 1.00 g of a water absorbent or a water absorbent resin was added, and the solution was stirred for 16 hours by using a stirring vane having a 40 mm length and a 8 mm diameter (for example, stirring vane A, product of Sougo Rikagaku Glass Seisakusho Co., Ltd.) and a magnetic stirrer so that a depth of its whirlpool was approximately 2 cm. In this way, a soluble component of the water absorbent or the water absorbent resin was extracted. The extract solution was filtered through a piece of filter paper (product of Advantec Toyo Kaisha, Ltd.; product name: JIS P3801, No. 2; thickness: 0.26 mm; diameter of retained particles: 5 μm), thereby obtaining a filtrate. 50.0 g of the filtrate was measured, and used as a measurement solution.

Next, the physiological saline to which the water absorbent or the water absorbent resin had not been added was titrated by using a 0.1N NaOH solution, until pH of the physiological saline reached 10. After that, the physiological saline was titrated by using a 0.1N HCl solution, until pH of the physiological saline reached 2.7. In this way, empty titration amounts ([bNaOH]ml and [bHCl]ml) were measured.

The same operation was performed with respect to the measurement solution, thereby measuring titration amounts ([NaOH]ml and [HCl]ml).

Thereafter, in accordance with the empty titration amounts and the titration amounts of the measurement solution, a quantity of a soluble component in the water absorbent or the water absorbent resin was calculated. That is, for example, in case of a water absorbent or a water absorbent resin including a known amount of acrylic acid and its sodium chloride, it was possible to calculate a quantity of a soluble component in the water absorbent or the water absorbent resin, in accordance with the following (Equation 9), from an average molecular mass of the monomer and the titration amounts obtained by the foregoing operation.

Soluble amount (weight %)=$0.1 \times$(average molecular mass)$\times 184.3 \times 100 \times ([HCl]-[bHCl])/1000/1.0/50.0$ (Equation 9)

In case of using a water absorbent or a water absorbent rein constituted of a component whose amount was unknown, the average molecular mass of the monomer was calculated from a neutralization ratio calculated in accordance with the following (Equation 10), and a soluble component in the water absorbent or the water absorbent resin was calculated in accordance with the foregoing (Equation 9).

Neutralization ratio (mol %)=$(1-([NaOH]-[bNaOH])/([HCl]-[bHCl])) \times 100$ (Equation 10)

Note that, in case of (i) a water absorbent resin obtained by using an unsaturated monomer containing no carboxyl group and (ii) a water absorbent or a water absorbent resin whose properties cannot be measured by the foregoing method, a quantity of a water soluble component is measured in accordance with gravity measurement recited on column 23, lines 10 to 55 of U.S. Reissue Pat. No. Re37021.

[Solid Content Ratio and Moisture Content]

1.000 g of a water absorbent or a water absorbent resin was placed in the aforementioned aluminum cup (diameter: 52 mm), and was heated for three hours in a windless oven at 180° C. Then, a percentage of a solid component and a percentage of a moisture content were calculated from a drying loss of the water absorbent or the water absorbent resin. Note that, the drying loss was measured according to the method described in Japanese Publication for Unexamined Patent Application, Tokukai 2000-121291, page 13, paragraph [0069]. That is, the moisture content was calculated by performing the foregoing operation after leaving the water absorbent or the water absorbent resin for one hour under a condition of 25° C. and 90% RH relative humidity.

Here, the solid content is the water absorbent or the water absorbent resin from which a volatile component (mainly water) has been removed, that is, a pure resin component of the water absorbent or the water absorbent resin, and a ratio of a mass of the solid content (quantity of the solid content) to a mass of the water absorbent or the water absorbent resin having the volatile component is a solid content ratio (% by mass).

Further, the moisture content is a ratio (% by mass) of water, which is a main component of the volatile component contained in the water absorbent or the water absorbent resin, to the water absorbent or the water absorbent resin, and corresponds to a value obtained by subtracting the solid content ratio (% by mass) from 100(%).

[Evaluation of Absorbent Article (Return Amount and Diffusion Ratio)]

To an entire absorbent article, a 2.06 kPa load was applied. Then, the absorbent article was left at a room temperature. From a cylinder, having (i) a 50 mm diameter and a 100 mm height, which had been disposed at a center of the absorbent article, 75 g of physiological saline (a 0.9% by weight NaCl solution) adjusted to 37° C. was poured to the absorbent article. The absorbent article was left for three hours while the load was continually applied. Then, a paper towel (Kitchen Towel Extra Dry, product of Oji Paper Co., Ltd.; cut into 120 mm×450 mm pieces, 30 pieces layered)

was placed on the absorbent article, and a 37 g/cm² (3.63 kPa) load was applied thereon for one minute. Then, an amount of liquid returned to the paper towel was measured.

Subsequently, after the return amount was measured, a nonwoven front surface sheet (liquid-impermeable sheet) of the absorbent article was cut with a retractable knife. Then, a liquid-soaked area of a web inside the absorbent article was measured, and its ratio (percentage) to an area of the entire web was calculated as a diffusion ratio.

[Measurement of Maximum Insertion Load (PIL), Insertion Work (PIW), and Insertion Distance (PID)]

<Measurement Sample>

27 g to 30 g of a water absorbent or a water absorbent resin was placed in a glass cylindrical sample tube (external diameter is 35 mm, internal diameter is 33 mm, height is 78 mm: for example, Screw tube No. 7 made by Maruemu Corporation., or the like), and was sufficiently shaken. Thereafter, on an iron plate, the resultant was tapped upward and downward for one minute (three times per second, vibration amplitude is 10 mm), thereby closely filling the cylindrical sample tube with water absorbent or the water absorbent resin. Subsequently, by increasing or decreasing an amount of the water absorbent or the water absorbent resin as required, adjustment was performed so that a height of the water absorbent or the water absorbent resin closely filled in the cylindrical sample tube (hereinafter, such water absorbent or a water absorbent resin is referred to as a particle layer) was 45 mm±1.5 mm. In case where the amount of the water absorbent or the water absorbent resin was adjusted in this manner, the resultant was sufficiently shaken again. Thereafter, the resultant was tapped upward and downward for one minute (three times per second, vibration amplitude is 10 mm), thereby closely filling the sample tube with the water absorbent or the water absorbent resin. Note that, the tapping was performed so that an upper surface of the particle layer was flat and horizontal after the tapping.

Further, in measuring PIL, PIW, and PID, a value obtained by averaging values measured three times was adopted. Thus, the cylindrical sample tube in which the particle layer had been formed was covered with a lid and was sufficiently shaken each time of measurement, and the resultant was tapped upward and downward again on the iron plate for one minute as in the foregoing operation, thereby obtaining a measurement sample in which an upper surface of the particle layer was flat and horizontal.

<Measuring Device>

Measurement of PIL, PIW, and PID was performed by using a measuring device 10 (KES-G5 Handy Compression Tester: product of Kato-Tech. Co., Ltd, whose main office is located in Kyoto-shi, Minami-ku, Japan) shown in FIG. 1. The measuring device 10 includes: a compressor 11; a controller 12 for controlling the compressor 11; and a computer for fetching data obtained from the compressor 11 and the controller 12, wherein the compressor 11, the controller 12, and the computer 13 are connected to each other via cables.

Figure 2:
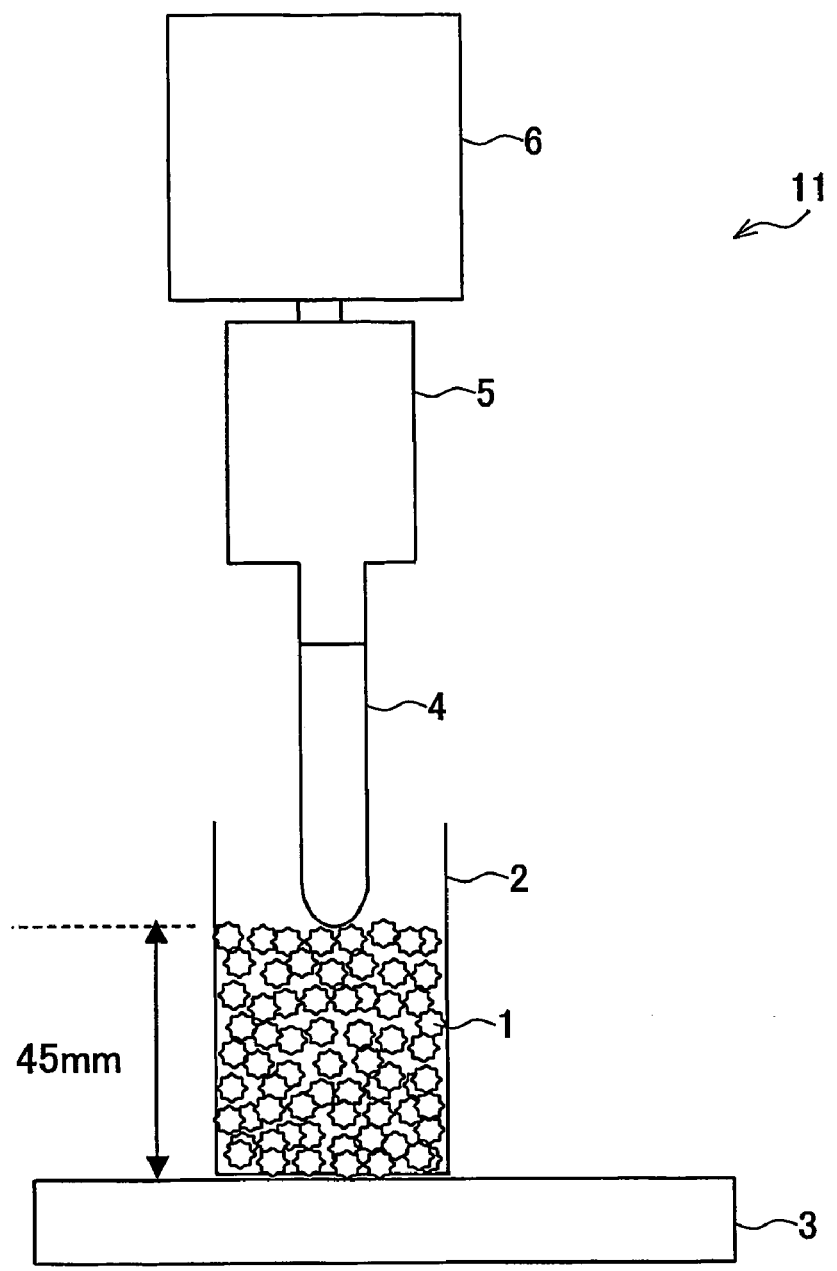
FIG. 2 is a front view showing an important portion of a compressor provided on the measuring device.

As shown in FIG. 2, the compressor 11 includes: a movable stage 3; an insertion probe (insertion member) 4; a movable load cell (force meter) 5; and a displacement distance detector 6.

Figure 3:
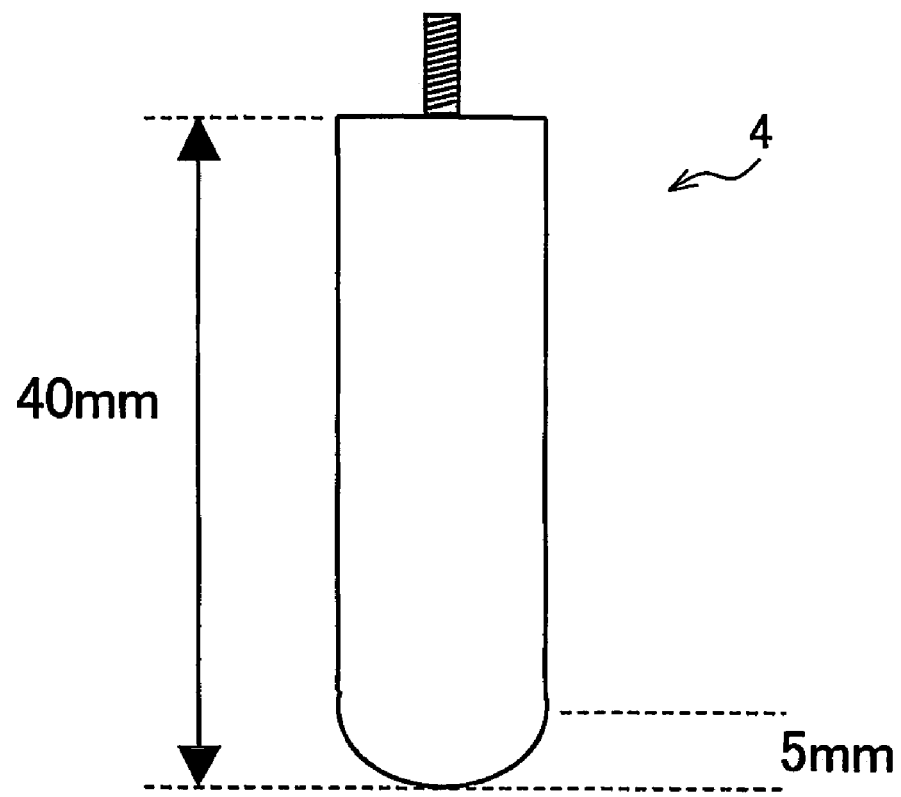
FIG. 3 is a front view showing an insertion probe provided on the compressor.

The stage 3 is a table on which a measurement sample 2 filled with a water absorbent or a water absorbent resin (hereinafter, a particle layer) 1 is placed, is movable forward and backward with respect to the insertion probe 4. Further, the insertion probe 4 is a metallic stick which is inserted into the particle layer 1 constituted of the water absorbent or the water absorbent resin filled in the measurement sample 2. In the present example, as shown in FIG. 3, the insertion probe 4 has a diameter of 12.7 mm and a length of 40 mm, and is made of anodized aluminum whose end portion is rounded so as to have a spherical surface with a 5 mm radius. Note that, as to the insertion probe 4, its surface roughness standardized on the basis of JISB0601-1994 has a maximum height of usually 0 to 10 μm, preferably 0 to 1 μm, and a 10-point-average roughness is 0 to 10 μm, preferably 0 to 1 μm, and a central-line-average roughness is 0 to 5 μm, preferably 0 to 1 μm. As shown in FIG. 3, the insertion probe 4 is fixed to the load cell 5 (FIG. 2) with a screw, and integrally moves with the load cell 5.

Further, the load cell 5 applies various loads, whose upper limit is 10 kg, to the particle layer 1 in the measurement sample 2 via the insertion probe 4. As shown in FIG. 2, the load cell 5 is connected to the displacement distance detector 6, and is provided so as to be movable forward and backward with respect to the measurement sample 2. The displacement distance detector 6 detects a displacement distance which is a distance at which the load cell 5 moves.

Moreover, the controller 12 shown in FIG. 1 includes: an insertion speed adjuster for adjusting a speed at which the insertion probe 4 is inserted; a load adjuster for adjusting a load applied from the insertion probe 4 to the particle layer of the measurement sample 2; a displacement distance adjuster for adjusting a displacement distance of the load cell 5; a displacement distance display for displaying a displacement distance of the load cell 5; a load display for displaying a load applied to the particle layer of the measurement sample 2; and an integration indicator.

Further, the computer 13 shown in FIG. 1 fetches data, obtained from the compressor 11 and the controller 12, as digital data. The computer 13 stores (i) a displacement distance of the insertion probe 4 (that is, the load cell 5) which is in contact with an upper surface of the particle layer 1 of the measurement sample 2 and (ii) a load applied to the particle layer 1.

<Measuring Condition and Measuring Method>

The measuring device 10 was placed on a horizontal testing table with no vibration, and measurement of PIL, PIW, and PID was performed as follows under a condition of a temperature of 25±1° C.) and 50±5% RH relative humidity.

That is, the measurement sample 2 was prepared in the aforementioned manner, and the measurement sample 2 was placed on the stage 3 of the compressor 11 (FIG. 1) of the measuring device 10 while giving least vibration thereto. Subsequently, the stage 3 was raised to and was fixed at such a position that an end portion of the insertion probe 4 shown in FIG. 2 touches the upper surface of the particle layer 1 in the measurement sample 2, and the position was defined as a starting point (0 mm).

Thereafter, the end portion of the insertion probe 4 was inserted into the particle layer 1 at an insertion speed of 1 mm per second. At the same time as commencement of the insertion of the insertion probe 4, the measurement was commenced so that data was read at intervals of 0.1 second, thereby measuring an insertion distance of the insertion probe 4 and a load which enabled insertion of the insertion probe 4. Note that, the insertion distance of the insertion probe 4 was within a range of from the starting point (0 mm) to 20 mm (within an error of 3%), and a maximum load within a range of from 0 to 20 mm insertion distance was a maximum insertion load (PIL).

Further, as shown in FIG. 4, a graph was made so that the measured insertion distance (mm) is indicated by a horizontal axis and the measured load (g-weight or g f) was indicated by a vertical axis, and an area (shaded area of FIG. 4) surrounded by a curve constituted of values of the obtained load and the horizontal axis was integrated within a range of from 0 to 20 mm insertion distance, thereby obtaining an insertion work (PIW) at which the insertion probe 4 was inserted within 0 to 20 mm insertion distance.

The foregoing operation was repeated three times so as to perform the measurement, and a value obtained by averaging thus three obtained values was regarded as a measurement value. As values of PIL and PIW determined in the foregoing manner are smaller, particles of the water absorbent or the water absorbent resin of the particle layer 1 may be regarded as having more excellent sliding properties, and may be regarded as being easier to handle.

Note that, in case where the load had becomes 10,000 g weight before the insertion distance of the insertion probe 4 reaches 20 mm, the fluidity of the powder may be regarded as being extremely low. Thus, evaluation was performed in terms of merely an insertion distance (PID) of the insertion probe 4. Note that, as to the water absorbent or the water absorbent resin evaluated in terms of merely PID, evaluation in terms of the following recovery index was not performed.

[Measurement of Recovery Index (RI)]

As to the measurement sample 2 in which the insertion distance of the insertion probe 4 reached 20 mm but the load did not reach 10,000 g-weight, a recovery index (RI) was calculated as follows.

That is, first measurement was performed under the same condition and in the same manner as in the measurement of PIL, PIW, and PID, and the insertion probe 4 inserted to 20 mm was pulled out from the particle layer 1 at the same speed as the insertion speed, and the insertion probe 4 was moved to the starting point (0 mm). Thereafter, the insertion probe 4 was inserted into the particle layer 1 again, without changing positions of the measurement sample 2 and the insertion probe 4, while keeping the same state as in pulling the insertion probe 4, under the same condition as in the first measurement. Then, displacement distances and loads were recorded at intervals of 0.1 per second from commencement of the measurement as in the first measurement. Note that, a time from completion of the first measurement to the commencement of the second measurement was within 15 seconds. During this time, the vibration given thereto was minimized.

As to the first measurement and the second measurement respectively, PIW was calculated in accordance with the aforementioned calculation method, and RI was calculated in accordance with the following (Equation 11).

$$\text{Recovery index RI (\%)}=(2^{nd}PIW/1^{st}PIW)\times 100 \quad \text{(Equation 11)},$$

where $1^{st}$PIW indicates PIW obtained in the first measurement, and $2^{nd}$PIW indicates PIW (reinsertion work) obtained in the second measurement.

The foregoing operation was repeated three times, and a value obtained by averaging thus obtained three values was a measurement value. As shown in FIG. 5, RI determined in the foregoing manner is an index indicative of a degree to which a void (an insertion mark made by the insertion probe 4) formed on the particle layer 1 by the first insertion of the insertion probe 4 is restored to a state before the insertion of the insertion probe 4.

That is, when RI=0%, as shown in FIG. 5, the insertion mark made by the insertion probe 4 is clearly observed in the particle layer 1 even after pulling out the insertion probe 4. In contrast, when RI=100%, as shown in FIG. 5, after pulling out the insertion probe 4, the void is recovered to a state before the first measurement in which the insertion probe 4 is inserted, so that the insertion mark made by the insertion probe 4 is not observed in the particle layer 1. Therefore, as RI approaches to 100%, the powder fluidity of the water absorbent or the water absorbent resin becomes more excellent.

Reference Example 1

5.9 g of polyethyleneglycoldiacrylate (average added mole number of ethylene oxide: 8) were dissolved in a 5500 g of a sodium acrylate solution (monomer concentration: 38% by weight) having a 65 mol % neutralization ratio, so as to prepare a reaction solution.

Then, the reaction solution was deaerated for 30 minutes in an atmosphere of nitrogen gas, and was fed to a reactor that had been prepared by placing a lid on a 10 L stainless-steel double-arm kneader equipped with two sigma vanes and a jacket. Inside the reactor was replaced with nitrogen gas while maintaining the temperature of the reaction solution at 30° C. Subsequently, 2.46 g of sodium persulfate and 0.10 g of L-ascorbic acid were added to the reaction solution, while the reaction solution was stirred. Approximately one minute later, polymerization was initiated. During the polymerization, the reaction solution was kept at 30° C. to 90° C. In 60 minutes after the polymerization was initiated, a water-containing gelled polymer was retrieved.

Thus obtained water-containing gelled polymer had been fragmented so that its diameter was approximately 5 mm. The water-containing gelled polymer fragmented was spread out on a wire mesh of 50 mesh (mesh size is 300 μm), and was dried by hot air at 150° C. for 90 minutes. A dry polymer thus obtained was crushed by using a vibrating mill, and then classified and blended by using a wire mesh of 20 meshes (mesh size is 850 μm). Thus, a water absorbent resin precursor (a) having a crushed indeterminate form was obtained.

In 100 parts of thus obtained water absorbent resin precursor (a), a surface cross-linking solvent including 0.5 parts of propyleneglycol, 0.3 parts of 1,4-butanediol, and three parts of water, was mixed. The mixture was then thermally processed at 200° C. for 45 minutes, thereby obtaining a water absorbent resin (A) whose surface had been cross-linked.

Examples 1 to 3

100 parts of the water absorbent resin (A) obtained in Reference example 1, and respectively 0.3 parts, 0.5 parts, and 1 part of zinc stearate were added into Lödige mixer (product of Gebr, Lödige Maschinenbau, GmbH; type: M5R) at 25° C. at 50% RH relative humidity. After stirring for 15 seconds at 330 rpm, water absorbents (1), (2), and (3) were respectively obtained therefrom.

As a result of photographic observation by means of a scanning-type electronic microscope, a particle diameter of thus added zinc stearate was approximately 10 μm or less. Further, a logarithmic standard deviation $\sigma\zeta$ of the water absorbents (1), (2), and (3) was 0.35, and a water absorbent resin whose particle diameter was not less than 300 μm was 63 mass % with respect to the entire water absorbent.

Examples 4 to 6

Except that calcium stearate (product of Kanto Kagaku) was used instead of the zinc stearate, the same operation as that of Examples 1 to 3 was performed, thereby obtaining water absorbents (4), (5), and (6).

As a result of photographic observation by means of a scanning-type electronic microscope, a particle diameter of thus added calcium stearate was approximately 10 μm or less. Further, a logarithmic standard deviation σζ of the water absorbents (4), (5), and (6) was 0.35, and a water absorbent resin whose particle diameter was not less than 300 μm was 63 mass % with respect to the entire water absorbent.

Example 7

With respect to 100 parts of the water absorbent resin precursor (a), which was obtained in Reference Example 1, 0.3 parts of zinc stearate (product of Kanto Kagaku) were added to the aforementioned Lödige mixer. Then, the mixture was stirred for 15 seconds at 330 rpm. Subsequently, a surface cross-linking agent including 0.5 parts of propyleneglycol, 0.3 part of 1,4-butanediol, and three parts of water, with respect to 100 parts of the water absorbent resin precursor (a), were added and mixed in the Lödige mixer. The mixture was then thermally processed at 200° C. for 45 minutes, thereby obtaining a water absorbent (7).

As a result of photographic observation by means of a scanning-type electronic microscope, zinc stearate whose particle diameter was 5 μm or less evenly adhered to a surface of the water absorbent resin. Further, a logarithmic standard deviation σζ of the water absorbent (7) was 0.40, and a water absorbent resin whose particle diameter was not less than 300 μm was 63 mass % with respect to the entire water absorbent.

Example 8

Except that 0.5 parts of zinc stearate was used, the same operation as that of Example 7 was performed, thereby obtaining a water absorbent (8).

Comparative Examples 1 and 2

Except that respectively 0.5 parts and 1 part of hydrophilic silicon dioxide (product name: Aerogil 200, product of Nippon Aerogil, Ltd.) were used instead of the zinc stearate, the same operation as that of Example 1 was performed, thereby obtaining comparative water absorbents (1) and (2).

Comparative Examples 3 and 4

Except that respectively 0.5 parts and 1 part of kaoline clay (Neogen DGH, product of Dry Branch Kaolin Company) were used instead of the zinc stearate, the same operation as that of Example 1 was performed, thereby obtaining comparative water absorbents (3) and (4).

Comparative Examples 5 to 7

Except that Sanwet IM1000 (product of Sanyo Chemical Industries, Ltd.), which was a starch-acrylic acid graft copolymer, was used instead of the water absorbent resin (A), and that respectively 1 part, three parts, and 10 parts of calcium stearate were used instead of the zinc stearate, the same operation as that of Example 1 was performed, thereby obtaining comparative water absorbents (5), (6), and (7). A logarithmic standard deviation σζ of the comparative water absorbents (5), (6), and (7) was 0.50.

Example 9

25 parts of the water absorbent (1) obtained in Example 1 and 75 parts of crushed wood pulp were dry-blended by using a mixer. Next, on a wire screen of 400 mesh (aperture: 38 μm), the mixture was shaped into a web of 120 mm×400 mm by using a batch-type air paper-producing apparatus. The web was then pressed for 5 seconds by applying a 194.14 kPa pressure, thereby obtaining an absorbent having an approximately 0.05 g/cm$^2$ basic weight.

Subsequently, (i) a so-called back surface sheet (liquid-impermeable sheet) made of impermeable polypropylene, (ii) the absorbent, and (iii) a nonwoven front surface sheet (liquid-permeable sheet) of liquid-permeable polypropylene were bonded with each other in this order by using a double-face adhesive tape. As a result, an absorbent article was obtained.

A weight of the absorbent article was 50 g. A return amount and a diffusion ratio of thus obtained absorbent article were 16.2 g and 90%, respectively.

Example 10

100 parts of the water absorbent resin (A) obtained in Reference example 1 and 0.01 parts of magnesium stearate (product of Kanto Kagaku) were placed into a polyethylene bag at 25° C. at 50% RH relative humidity. The mixture was sufficiently shaken and stirred for 20 minutes, thereby obtaining a water absorbent (9).

Further, in order to examine the powder fluidity under a condition of a high temperature, measurement of an insertion distance PID, a maximum insertion load PIL, an insertion work PIW, and a recovery index RI was performed under such a condition that a powder temperature of the water absorbent (9) was 70° C. to 80° C. That is, the obtained water absorbent (9) was filled in a cylindrical sample tube, and the cylindrical tube was covered with a lid. Thus sealed sample tube was left in an airless dryer, whose temperature was adjusted to 80° C., for three hours. After confirming that temperature of the water absorbent (9) in the sample tube became 80° C., the sample tube was pulled out from the airless dryer. The lid of the pulled out sample tube was opened, and the measurement of the insertion distance PID, the maximum insertion load PIL, the insertion work PIW, and the recovery index RI was performed in the aforementioned manner. Note that, the measurement was commenced within two minutes after pulling out the sample tube from the airless dryer.

The temperature of the water absorbent (9) at the time of measurement was 70° C. to 80° C., and the insertion distance PID was 20 mm, and the maximum insertion load PIL was 450 g-weight, and the insertion work was 4300 g-weight× mm, and the recovery index PI was 77%.

Example 11

100 parts of the water absorbent resin (A) obtained in Reference example 1 and 0.01 parts of calcium palmitate (product of Kanto Kagaku) were placed into a polyethylene bag at 25° C. at 50% RH relative humidity. The mixture was sufficiently shaken and stirred for 20 minutes, thereby obtaining a water absorbent (10).

Example 12

100 parts of the water absorbent resin (A) obtained in Reference example 1, 0.2 parts of aluminum monostearate (structural formula: $Al(OH)_2(C_{17}H_{35}COO)$), and 0.1 part of kaoline clay were placed into a polyethylene bag at 25° C. at 50% RH relative humidity. The mixture was sufficiently shaken and stirred for 20 minutes, thereby obtaining a water absorbent (11).

Comparative Example 8

With respect to 100 parts of the water absorbent resin (A) obtained in Reference Example 1, 0.1 part of polyethyleneglycol (its molecular weight is 400: product of Kanto Kagaku) was added, thereby obtaining a comparative water absorbent (8).

Comparative Example 9

Except that a comparative water absorbent (1) was used instead of the water absorbent (1), the same operation as that of Example 9 was performed, thereby obtaining a comparative absorbent article.

A weight of the comparative absorbent article was 50 g. A return amount and a diffusion ratio of thus obtained comparative absorbent article were 19.5 g and 86%, respectively.

Reference Example 2

Except that a 5500 g of a sodium acrylate solution (monomer concentration: 35% by weight) having a 75 mol % neutralization ratio was used instead of the sodium acrylate solution having the 65 mol % neutralization ratio, and that an amount of polyethyleneglycoldiacrylate (average added mole number of ethylene oxide: 8) to be used was 2.8 g (0.025 mol %), the same operation as that of Reference Example 1 was performed, thereby obtaining a water absorbent resin precursor (b) having a crushed indeterminate form.

In 100 parts of thus obtained water absorbent resin precursor (b), a surface cross-linking solvent including 0.3 parts of ethyleneglycolglycidylether, 0.5 parts of propylene glycol, 0.3 parts of 1,4-butanediol, and three parts of water, was mixed. The mixture was then thermally processed at 200° C. for 40 minutes, thereby obtaining a water absorbent resin (B) whose surface had been cross-linked.

Example 13

100 parts of the water absorbent resin (B) obtained in Reference example 2, and 0.3 parts of aluminum stearate (structural formula: $Al(C_{17}H_{35}COO)_3$, product of Wako Pure Chemical Industries, Ltd.) were added into Lödige mixer (product of Gebr, Lödige Maschinenbau, GmbH; type: M5R) at 25° C. at 50% RH relative humidity. After stirring for 15 seconds at 330 rpm, thereby obtaining a water absorbent (12).

[Results]

As to thus obtained water absorbent resins (A) and (B), thus obtained water absorbents (1) to (12), thus obtained comparative water absorbents (1) to (8), Table 1 shows (i) a ratio (wt %) of particles whose particle diameter ranges from 106 μm or more to less than 850 μm, (ii) a weight (mass) average particle diameter (D50 (μm)), (iii) an absorbency without pressure (GV), and (iv) a water-soluble component (soluble amount (%)).

Further, Table 2 shows a moisture content at the time of moisture absorption, a moisture absorption fluidity index, a moisture absorption fluidity retention index, before and after applying a shock. Moreover, Table 3 shows absorbencies under pressure AAP1 (g/g) and AAP2 (g/g), and first and second absorbency-under-pressure retention indexes, before and after applying a shock. Further, Table 4 shows an insertion distance PID, a maximum insertion load PIL, an insertion work PIW, and a recovery index RI, before and after applying a shock, under a condition of 25° C.

TABLE 1

| | RATIO OF PARTICLES HAVING DIAMETERS IN A RANGE OF 106 μm TO 850 μm(wt %) | D50(μm) | GV(g/g) | QUANTITY OF SOLUBLE COMPONENT(%) |
|---|---|---|---|---|
| WATER ABSORBENT (1) | 95 | 368 | 34.7 | 17.0 |
| WATER ABSORBENT (2) | 95 | 370 | 35.4 | 17.0 |
| WATER ABSORBENT (3) | 95 | 370 | 34.0 | 17.0 |
| WATER ABSORBENT (4) | 96 | 370 | 35.0 | 17.0 |
| WATER ABSORBENT (5) | 94 | 370 | 35.0 | 17.0 |
| WATER ABSORBENT (6) | 96 | 370 | 34.0 | 17.0 |
| WATER ABSORBENT (7) | 96 | 374 | 35.0 | 17.0 |
| WATER ABSORBENT (8) | 97 | 375 | 34.0 | 18.0 |
| WATER ABSORBENT (9) | 95 | 370 | 34.0 | 17.0 |
| WATER ABSORBENT (10) | 95 | 370 | 34.0 | 17.0 |
| WATER ABSORBENT (11) | 95 | 370 | 34.0 | 17.0 |
| WATER ABSORBENT (12) | 97 | 440 | 42.0 | 25.0 |
| WATER ABSORBENT RESIN (A) | 95 | 365 | 35.1 | 18.0 |
| WATER ABSORBENT RESIN (B) | 97 | 440 | 42.0 | 25.0 |
| COMPARATIVE WATER ABSORBENT (1) | 95 | 366 | 35.4 | 17.0 |
| COMPARATIVE WATER ABSORBENT (2) | 95 | 365 | 34.7 | 17.0 |
| COMPARATIVE WATER ABSORBENT (3) | 96 | 368 | 33.5 | 17.0 |
| COMPARATIVE WATER ABSORBENT (4) | 96 | 372 | 33.4 | 18.0 |
| COMPARATIVE WATER ABSORBENT (5) | 80 | 310 | 47.4 | 12.2 |
| COMPARATIVE WATER ABSORBENT (6) | 80 | 310 | 46.6 | 12.0 |

TABLE 1-continued

|  | RATIO OF PARTICLES HAVING DIAMETERS IN A RANGE OF 106 μm TO 850 μm(wt %) | D50(μm) | GV(g/g) | QUANTITY OF SOLUBLE COMPONENT(%) |
|---|---|---|---|---|
| COMPARATIVE WATER ABSORBENT (7) | 80 | 305 | 46.5 | 13.0 |
| COMPARATIVE WATER ABSORBENT (8) | 94 | 370 | 34.5 | 17.0 |

TABLE 2

|  | MOISTURE CONTENT AT THE TIME OF MOISTURE ABSORPTION(%) | MOISTURE ABSORPTION FLUIDITY INDEX BEFORE SHOCK IS APPLIED | MOISTURE ABSORPTION FLUIDITY INDEX AFTER SHOCK IS APPLIED | MOISTURE ABSORPTION FLUIDITY RETENTION INDEX |
|---|---|---|---|---|
| WATER ABSORBENT (1) | 23 | 99.3 | 100.0 | 1.01 |
| WATER ABSORBENT (2) | 22 | 100.0 | 100.0 | 1.00 |
| WATER ABSORBENT (3) | 24 | 100.0 | 100.0 | 1.00 |
| WATER ABSORBENT (4) | 23 | 99.3 | 100.0 | 1.01 |
| WATER ABSORBENT (5) | 18 | 100.0 | 100.0 | 1.00 |
| WATER ABSORBENT (6) | 19 | 100.0 | 100.0 | 1.00 |
| WATER ABSORBENT (7) | 25 | 93.0 | 92.0 | 0.99 |
| WATER ABSORBENT (8) | 24 | 100.0 | 100.0 | 1.00 |
| WATER ABSORBENT (9) | 23 | 25.0 | 14.0 | 0.56 |
| WATER ABSORBENT (10) | 16 | 27.0 | 15.0 | 0.56 |
| WATER ABSORBENT (11) | 18 | 91.0 | 94.0 | 1.03 |
| WATER ABSORBENT (12) | 20 | 94.0 | 98.0 | 1.04 |
| WATER ABSORBENT RESIN (A) | 20 | 46.3 | 10.6 | 0.23 |
| WATER ABSORBENT RESIN (B) | 21 | 16.3 | 3.0 | 0.18 |
| COMPARATIVE WATER ABSORBENT (1) | 25 | 90.0 | 43.0 | 0.48 |
| COMPARATIVE WATER ABSORBENT (2) | 23 | 88.1 | 79.7 | 0.90 |
| COMPARATIVE WATER ABSORBENT (3) | 22 | 95.8 | 42.0 | 0.44 |
| COMPARATIVE WATER ABSORBENT (4) | 23 | 94.9 | 86.7 | 0.91 |
| COMPARATIVE WATER ABSORBENT (5) | 24 | 45.7 | 46.0 | 1.01 |
| COMPARATIVE WATER ABSORBENT (6) | 23 | 82.0 | 85.0 | 1.04 |
| COMPARATIVE WATER ABSORBENT (7) | 25 | 88.5 | 89.1 | 1.01 |
| COMPARATIVE WATER ABSORBENT (8) | 21 | 18.0 | 5.0 | 0.28 |

TABLE 3

|  | AAP1 BEFORE SHOCK IS APPLIED(g/g) | AAP1 AFTER SHOCK IS APPLIED(g/g) | APPLIED-PRESSURE ABSORPTION RETENTION INDEX 1 | AAP2 BEFORE SHOCK IS APPLIED(g/g) | AAP2 AFTER SHOCK IS APPLIED(g/g) | APPLIED-PRESSURE ABSORPTION RETENTION INDEX 2 |
|---|---|---|---|---|---|---|
| WATER ABSORBENT (1) | 32.1 | 31.1 | 0.97 | 20.2 | 19.2 | 0.95 |
| WATER ABSORBENT (2) | 34.3 | 32.9 | 0.96 | 19.7 | 19.2 | 0.97 |
| WATER ABSORBENT (3) | 34.1 | 33.0 | 0.97 | 19.9 | 19.6 | 0.98 |
| WATER ABSORBENT (4) | 32.1 | 31.1 | 0.97 | 22.0 | 19.6 | 0.89 |
| WATER ABSORBENT (5) | 32.2 | 30.9 | 0.96 | 20.1 | 19.5 | 0.97 |
| WATER ABSORBENT (6) | 32.4 | 31.1 | 0.96 | 19.6 | 19.4 | 0.99 |
| WATER ABSORBENT (7) | 32.2 | 31.4 | 0.98 | 19.6 | 19.4 | 0.99 |
| WATER ABSORBENT (8) | 33.3 | 33.1 | 0.99 | 19.8 | 19.7 | 0.99 |
| WATER ABSORBENT (9) | 33.4 | 32.7 | 0.98 | 22.1 | 20.0 | 0.90 |
| WATER ABSORBENT (10) | 33.7 | 32.2 | 0.96 | 22.4 | 20.3 | 0.91 |
| WATER ABSORBENT (11) | 32.9 | 32.7 | 0.99 | 22.2 | 21.0 | 0.95 |
| WATER ABSORBENT (12) | 31.0 | 28.2 | 0.91 | 19.5 | 17.7 | 0.91 |
| WATER ABSORBENT RESIN (A) | 35.1 | 30.9 | 0.88 | 23.0 | 19.9 | 0.87 |
| WATER ABSORBENT RESIN (B) | 36.1 | 31.1 | 0.86 | 21.5 | 18.3 | 0.85 |
| COMPARATIVE WATER ABSORBENT (1) | 29.1 | 19.9 | 0.68 | 15.5 | 13.7 | 0.88 |

TABLE 3-continued

|  | AAP1 BEFORE SHOCK IS APPLIED(g/g) | AAP1 AFTER SHOCK IS APPLIED(g/g) | APPLIED-PRESSURE ABSORPTION RETENTION INDEX 1 | AAP2 BEFORE SHOCK IS APPLIED(g/g) | AAP2 AFTER SHOCK IS APPLIED(g/g) | APPLIED-PRESSURE ABSORPTION RETENTION INDEX 2 |
|---|---|---|---|---|---|---|
| COMPARATIVE WATER ABSORBENT (2) | 28.4 | 18.7 | 0.66 | 14.9 | 12.2 | 0.82 |
| COMPARATIVE WATER ABSORBENT (3) | 29.9 | 20.8 | 0.70 | 16.0 | 13.0 | 0.81 |
| COMPARATIVE WATER ABSORBENT (4) | 27.3 | 21.1 | 0.77 | 12.0 | 11.0 | 0.92 |
| COMPARATIVE WATER ABSORBENT (5) | 15.0 | 14.0 | 0.93 | 12.0 | 11.0 | 0.92 |
| COMPARATIVE WATER ABSORBENT (6) | 16.3 | 14.2 | 0.87 | 13.0 | 12.0 | 0.92 |
| COMPARATIVE WATER ABSORBENT (7) | 17.0 | 16.9 | 0.99 | 15.0 | 14.0 | 0.93 |
| COMPARATIVE WATER ABSORBENT (8) | 32.5 | 28.6 | 0.88 | 23.1 | 20.0 | 0.87 |

TABLE 4

|  | AAP1 BEFORE SHOCK IS APPLIED (g/g) | BEFORE SHOCK IS APPLIED | | | | AFTER SHOCK IS APPLIED | | | |
|---|---|---|---|---|---|---|---|---|---|
|  |  | PID mm | PIL g weight | PIW g weight × mm | RI % | PID mm | PIL g weight | PIW g weight × mm | RI % |
| WATER ABSORBENT (1) | 32.1 | 20 | 337 | 3050 | 75 | 20 | 276 | 2500 | 76 |
| WATER ABSORBENT (2) | 34.3 | 20 | 337 | 3050 | 75 | 20 | 276 | 2500 | 76 |
| WATER ABSORBENT (3) | 34.1 | 20 | 315 | 2950 | 76 | 20 | 270 | 2450 | 76 |
| WATER ABSORBENT (4) | 32.1 | 20 | 294 | 2750 | 71 | 20 | 310 | 2900 | 72 |
| WATER ABSORBENT (5) | 32.2 | 20 | 315 | 2950 | 76 | 20 | 270 | 2450 | 76 |
| WATER ABSORBENT (6) | 32.4 | 20 | 273 | 2400 | 75 | 20 | 235 | 2200 | 76 |
| WATER ABSORBENT (7) | 32.2 | 20 | 397 | 3800 | 76 | 20 | 200 | 1950 | 76 |
| WATER ABSORBENT (8) | 33.3 | 20 | 334 | 3000 | 72 | 20 | 210 | 1900 | 74 |
| WATER ABSORBENT (9) | 33.4 | 20 | 510 | 4800 | 77 | 20 | 285 | 2750 | 76 |
| WATER ABSORBENT (10) | 33.7 | 20 | 450 | 4250 | 75 | 20 | 235 | 2050 | 76 |
| WATER ABSORBENT (11) | 32.9 | 20 | 425 | 4050 | 68 | 20 | 410 | 3800 | 71 |
| WATER ABSORBENT (12) | 32.5 | 20 | 260 | 2450 | 72.0 | 20.0 | 207 | 1950 | 73 |
| WATER ABSORBENT RESIN (A) | 35.1 | 9 | over10000 | — | — | 9.3 | over10000 | — | — |
| WATER ABSORBENT RESIN (B) | 36.1 | 11 | over10000 | — | — | 11 | over10000 | — | — |
| COMPARATIVE WATER ABSORBENT (1) | 29.1 | 7.7 | over10000 | — | — | 8 | over10000 | — | — |
| COMPARATIVE WATER ABSORBENT (2) | 28.4 | 6.8 | over10000 | — | — | 7.1 | over10000 | — | — |
| COMPARATIVE WATER ABSORBENT (3) | 29.9 | 7.2 | over10000 | — | — | 7.4 | over10000 | — | — |
| COMPARATIVE WATER ABSORBENT (4) | 27.3 | 6.5 | over10000 | — | — | 6.7 | over10000 | — | — |
| COMPARATIVE WATER ABSORBENT (5) | 15 | 20 | 315 | 2950 | 76 | 20 | 270 | 2450 | 76 |
| COMPARATIVE WATER ABSORBENT (6) | 16.3 | 20 | 294 | 2750 | 71 | 20 | 310 | 2900 | 72 |
| COMPARATIVE WATER ABSORBENT (7) | 17 | 20 | 315 | 2950 | 76 | 20 | 270 | 2450 | 76 |
| COMPARATIVE WATER ABSORBENT (8) | 32.5 | 20 | 2750 | 20000 | 8 | 20 | 2545 | 20150 | 9 |

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

The particulate water absorbent of the present invention has excellent fluidity at the time of moisture absorption and excellent absorbent properties, so that the particulate water absorbent can be used as various kinds of absorbent articles. Specifically, it is possible to preferably use the particulate water absorbent as a sanitary material, such as an adult paper diaper, a child diaper, a sanitary napkin, and a so-called incontinence pad, that has been greatly developed recently. When the absorbent article of the present invention is used, it is possible to reduce an amount of an absorbed aqueous liquid which returns from the particulate water absorbent contained in the absorbent article, so that an excellent dry condition is kept after absorbing water. As a result, it is possible to reduce loads of a user wearing the absorbent article and caregivers.

The invention claimed is:

1. A particulate water absorbent, comprising a water absorbent resin in which a polymer obtained by polymerizing an unsaturated monomer has a cross-linking structure therein, wherein:
   the water absorbent resin is a particulate water absorbent resin which has a cross-linking structure on a surface thereof, and is constituted of particles each of which has a shape other than a shape of a spherical primary particle and a shape of an ellipsoidal primary particle,
   the particulate water absorbent contains not less than 90 mass % of particles, whose particle diameter is not less than 106 μm and less than 850 μm, with respect to the particulate water absorbent,
   the particle size distribution of the water absorbent is from 0 to 0.40, and
   the particulate water absorbent further contains not less than 0.001 mass % and less than 10 mass % of organic acid multivalent metal salt, whose molecule contains not less than seven carbon atoms, with respect to the water absorbent resin,
   wherein when the particulate water absorbent is immersed in 0.9 mass % of a sodium chloride aqueous liquid under a pressure of 2.06 kPa, an absorbency under pressure is not less than 20 g/g.

2. The particulate water absorbent as set forth in claim 1, wherein organic acid constituting the organic acid multivalent metal salt is a fatty acid.

3. The particulate water absorbent as set forth in claim 2, wherein the fatty acid is at least one kind of organic acid multivalent metal salt selected from a group of a capronic acid, an octanoic acid, an octynoate, a decanoic acid, a lauryl acid, a myristic acid, a palmitic acid, an oleic acid, and a stearic acid.

4. The particulate water absorbent as set forth in claim 1, wherein multivalent metal constituting the organic acid multivalent metal salt is alkaline earth metal and/or bivalent or multivalent transition metal.

5. The particulate water absorbent as set forth in claim 4, wherein alkaline earth metal and/or bivalent or multivalent transition metal is at least one kind selected from a group of barium, calcium, magnesium, aluminum, and zinc.

6. The particulate water absorbent as set forth in claim 1, wherein:
a melting point of the organic acid multivalent metal salt ranges from 40° C. to 250° C., and
the organic acid multivalent metal salt's solubility with respect to deionized water 1 L at 25° C. ranges from not less than 0 g/L to less than 5 g/L.

7. The particulate water absorbent as set forth in claim 1, wherein the organic acid multivalent metal salt adheres to a surface of the water absorbent resin.

8. The particulate water absorbent as set forth in claim 1, wherein:
a first absorbency-under-pressure retention index defined by (Equation 2) below and/or a second absorbency-under-pressure retention index defined by (Equation 3) below is not less than 0.90, $$\text{the first absorbency-under-pressure retention index} = Q1/P1 \quad \text{(Equation 2)},$$

where P1 is an absorbency under pressure of 2.06 kPa before applying a predetermined shock, and Q1 is an absorbency under pressure of 2.06 kPa after applying the predetermined shock, $$\text{the second absorbency-under-pressure retention index} = Q2/P2 \quad \text{(Equation 3)},$$

where P2 is an absorbency under pressure of 4.83 kPa before applying the predetermined shock, and Q2 is an absorbency under pressure of 4.83 kPa after applying the predetermined shock.

9. The particulate water absorbent as set forth in claim 1, wherein the unsaturated monomer contains an acrylic acid and/or salt thereof.

10. A sanitary material for absorbing a body fluid, comprising the particulate water absorbent as set forth in claim 1.

11. The sanitary material as set forth in claim 10, wherein the body fluid is at least one of feces, urine, blood.

12. A particulate water absorbent, comprising a water absorbent resin in which a polymer obtained by polymerizing an unsaturated monomer has a cross-linking structure therein, wherein:
the water absorbent resin is a particulate water absorbent resin which has a cross-linking structure on a surface thereof and is constituted of particles each of which has a shape other than a shape of a spherical primary particle and a shape of an ellipsoidal primary particle,
the particle size distribution of the water absorbent is from 0 to 0.4,
the particulate water absorbent further contains not less than 0.001 mass % and less than 10 mass % of organic acid multivalent metal salt, whose molecule contains not less than seven carbon atoms, with respect to the water absorbent resin, and
a moisture absorption fluidity index ranges from not less than 90 mass % to not more than 100 mass %,
wherein when the particulate water absorbent is immersed in 0.9 mass % of a sodium chloride aqueous liquid under a pressure of 2.06 kPa, an absorbency under pressure is not less than 20 g/g.

13. A particulate water absorbent, comprising a water absorbent resin in which a polymer obtained by polymerizing an unsaturated monomer has a cross-linking structure therein, wherein:
the water absorbent resin is a particulate water absorbent resin which has a cross-linking structure on a surface thereof and is constituted of particles each of which has a shape other than a shape of a spherical primary particle and a shape of an ellipsoidal primary particle;
the particle size distribution of the water absorbent is from 0 to 0.40,
a moisture absorption fluidity index X indicative of a moisture absorption fluidity before a shock is applied ranges from not less than 90 mass % to not more than 100 mass %, and
a moisture absorption fluidity retention index defined by (Equation 1) below is not less than 0.95, $$\text{the moisture absorption fluidity retention index} = Y/X \quad \text{(Equation 1)},$$

where X is the moisture absorption fluidity index X and Y is a moisture absorption fluidity index Y after applying a predetermined shock to the particulate water absorbent,
wherein when the particulate water absorbent is immersed in 0.9 mass % of a sodium chloride aqueous liquid under a pressure of 2.06 kPa, an absorbency under pressure is not less than 20 g/g.

14. The particulate water absorbent as set forth in claim 13, further comprising not less than 0.001 mass % and less than 10 mass % of organic acid multivalent metal salt, whose molecule contains not less than seven carbon atoms, with respect to the water absorbent resin.

15. A particulate water absorbent, comprising a water absorbent resin in which a polymer obtained by polymerizing an unsaturated monomer has a cross-linking structure therein, wherein:
the water absorbent resin is a water absorbent resin constituted of particles each of which has a shape other than a shape of a spherical primary particle and a shape of an ellipsoidal primary particle, and
the particle size distribution of the water absorbent is from 0 to 0.40, and
when the particulate water absorbent is immersed in 0.9 mass % of a sodium chloride aqueous liquid under a pressure of 2.06 kPa, an absorbency under pressure is not less than 20 g/g, and
a maximum insertion load which is a maximum load required in inserting an insertion probe to a predetermined distance of the particulate water absorbent is not less than 0 g-weight and not more than 1,000 g-weight, and
an insertion work which is a work in inserting the insertion probe to the predetermined distance of the particulate water absorbent is not less than 0 g-weight×mm and not more than 10,000 g-weight×mm.

16. The particulate water absorbent as set forth in claim 15, further comprising not less than 0.001 mass % and less than 10 mass % of organic acid multivalent metal salt, whose molecule contains not less than seven carbon atoms, with respect to the water absorbent resin.

17. The particulate water absorbent as set forth in claim 15, wherein the particulate water absorbent contains not less than 90 mass % of particles, whose particle diameter is not less than 106 μm and less than 850 μm, with respect to the particulate water absorbent.

18. The particulate water absorbent as set forth in claim 15, wherein the water absorbent resin has a cross-linking structure on a surface thereof.

19. A particulate water absorbent, comprising a water absorbent resin in which a polymer obtained by polymerizing an unsaturated monomer has a cross-linking structure therein, wherein:
  the water absorbent resin is a water absorbent resin constituted of particles each of which has a shape other than a shape of a spherical primary particle and a shape of an ellipsoidal primary particle, and
  the particle size distribution of the water absorbent is from 0 to 0.40, and
  when the particulate water absorbent is immersed in 0.9 mass % of a sodium chloride aqueous liquid under a pressure of 2.06 kPa, an absorbency under pressure is not less than 20 g/g, and
  an insertion work which is a work in inserting the insertion probe to the predetermined distance of the particulate water absorbent is not less than 0 g-weight×mm and not more than 5,000 g-weight×mm, and
  a recovery index represented by a ratio of (i) a reinsertion work, which is a work in pulling out and reinserting the insertion probe after inserting the insertion probe to the predetermined distance of the particulate water absorbent, with respect to (ii) the insertion work is not less than 55%.

20. A method of producing a particulate water absorbent, including a water absorbent resin in which a polymer obtained by polymerizing an unsaturated monomer has a cross-linking structure therein,
  the water absorbent resin being constituted of particles each of which has a shape other than a shape of a spherical primary particle and a shape of an ellipsoidal primary particle, and the particle size distribution of the water absorbent is from 0 to 0.40, and
  said method comprising the step of adding organic acid multivalent metal salt, whose molecule contains not less than seven carbon atoms, to the water absorbent resin in and/or after cross-linking a surface of the water absorbent resin,
  whereby when the particulate water absorbent is immersed in 0.9 mass % of a sodium chloride aqueous liquid under a pressure of 2.06 kPa, an absorbency under pressure is not less than 20 g/g.

* * * * *